(12) United States Patent
Quintanar

(10) Patent No.: US 12,226,565 B2
(45) Date of Patent: *Feb. 18, 2025

(54) WOUND THERAPY SYSTEMS AND METHODS WITH MULTIPLE POWER SOURCES

(71) Applicant: T.J.Smith and Nephew, Limited, Hull (GB)

(72) Inventor: Felix Clarence Quintanar, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/635,962

(22) Filed: Apr. 15, 2024

(65) Prior Publication Data
US 2024/0342356 A1    Oct. 17, 2024

Related U.S. Application Data

(63) Continuation of application No. 17/414,729, filed as application No. PCT/EP2019/085271 on Dec. 16, 2019, now Pat. No. 11,969,538.

(30) Foreign Application Priority Data

Dec. 21, 2018   (GB) .................................. 1820927

(51) Int. Cl.
*A61M 1/00*    (2006.01)
*A61M 1/16*    (2006.01)

(52) U.S. Cl.
CPC ................ *A61M 1/73* (2021.05); *A61M 1/91* (2021.05); *A61M 1/915* (2021.05); *A61M 1/916* (2021.05);
(Continued)

(58) Field of Classification Search
CPC ...... A61M 1/91; A61M 1/96; A61M 2205/16; A61M 2205/8206; A61M 2205/8237;
(Continued)

(56) References Cited

U.S. PATENT DOCUMENTS 3,599,639 A    8/1971   Spotz
3,896,802 A    7/1975   Williams
(Continued)

FOREIGN PATENT DOCUMENTS

CN    105232229 A    1/2016
CN    105395184 A    3/2016
(Continued)

OTHER PUBLICATIONS

Aubakir B., et al., "Vital Sign Monitoring Utilizing Eulerian Video Magnification and Thermography," 38th Annual International Conference of the IEEE Engineering in Medicine and Biology Society, Aug. 16, 2016, pp. 3527-3530 (4 pages).
(Continued)

*Primary Examiner* — Guy K Townsend
*Assistant Examiner* — Seth Han
(74) *Attorney, Agent, or Firm* — Knobbe, Martens, Olson & Bear, LLP

(57) ABSTRACT

The present disclosure provides in part improved apparatuses, systems, and methods for providing therapy to a wound. A system can include a first power source configured to power an electronic component and a second power source configured to power the electronic component in place of the first power source. Responsive to a first condition, the second power source can power the electronic component in place of the first power source. In some cases, the system can include a pressure source that is configured to provide negative pressure to a wound dressing positioned (Continued)

over a wound. The wound dressing can support the first power source or the second power source.

20 Claims, 18 Drawing Sheets

(52) U.S. Cl.
CPC ............... *A61M 1/95* (2021.05); *A61M 1/96* (2021.05); *A61M 1/962* (2021.05); *A61M 1/985* (2021.05); *A61M 2205/16* (2013.01); *A61M 2205/8206* (2013.01); *A61M 2205/8237* (2013.01)

(58) Field of Classification Search
CPC ...... A61M 2205/82; A61M 2205/8212; A61B 2560/0204; A61B 2560/0209
See application file for complete search history.

(56) References Cited

U.S. PATENT DOCUMENTS

| | | |
|---|---|---|
| 4,334,530 A | 6/1982 | Hassell |
| 5,090,410 A | 2/1992 | Saper et al. |
| 5,177,371 A * | 1/1993 | Faulk ..................... H02J 9/06 340/636.15 |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,077,832 B2 | 7/2006 | Fleischmann |
| 7,088,591 B2 | 8/2006 | Kishimoto et al. |
| 7,201,063 B2 | 4/2007 | Taylor |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,569,742 B2 | 8/2009 | Haggstrom et al. |
| 7,625,117 B2 | 12/2009 | Haslett et al. |
| 7,687,678 B2 | 3/2010 | Jacobs |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,238,996 B2 | 8/2012 | Burnes et al. |
| 8,241,231 B2 | 8/2012 | Bausewein et al. |
| 8,332,053 B1 | 12/2012 | Patterson et al. |
| 8,333,874 B2 | 12/2012 | Currie |
| 8,366,692 B2 | 2/2013 | Weston et al. |
| 8,480,641 B2 | 7/2013 | Jacobs |
| 8,579,872 B2 | 11/2013 | Coulthard et al. |
| 8,644,911 B1 | 2/2014 | Panasyuk et al. |
| 8,663,106 B2 | 3/2014 | Stivoric et al. |
| 8,682,442 B2 | 3/2014 | McAdams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,220,455 B2 | 12/2015 | Sarrafzadeh et al. |
| 9,226,402 B2 | 12/2015 | Hsu |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Macia et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,907,103 B2 | 2/2018 | Chen et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov et al. |
| 10,152,789 B2 | 12/2018 | Carnes et al. |
| 10,182,740 B2 | 1/2019 | Tonar et al. |
| 10,207,031 B2 | 2/2019 | Toth |
| 10,209,213 B2 | 2/2019 | Kang et al. |
| 10,285,620 B2 | 5/2019 | Jung et al. |
| 10,321,862 B2 | 6/2019 | Dalene et al. |
| 10,463,773 B2 | 11/2019 | Haggstrom et al. |
| 10,687,984 B2 | 6/2020 | Rovaniemi |
| 10,857,038 B2 | 12/2020 | Zamierowski et al. |
| 11,026,847 B2 | 6/2021 | Piotrowski et al. |
| 11,647,922 B2 | 5/2023 | Scherer |
| 11,850,121 B2 | 12/2023 | Rapp |
| 2002/0016536 A1 | 2/2002 | Benni |
| 2002/0135752 A1 | 9/2002 | Sokolov et al. |
| 2003/0033032 A1 | 2/2003 | Lind et al. |
| 2003/0208148 A1 | 11/2003 | Sullivan |
| 2003/0210810 A1 | 11/2003 | Gee et al. |
| 2003/0216630 A1 | 11/2003 | Jersey-Willuhn et al. |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2006/0052678 A1 | 3/2006 | Drinan et al. |
| 2006/0058690 A1 | 3/2006 | Bartnik et al. |
| 2006/0181791 A1 | 8/2006 | Van Beek et al. |
| 2006/0234383 A1 | 10/2006 | Gough |
| 2006/0241495 A1 | 10/2006 | Kurtz |

(56) References Cited

U.S. PATENT DOCUMENTS

| | | |
|---|---|---|
| 2007/0040449 A1 | 2/2007 | Spurlin et al. |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0219597 A1 | 9/2007 | Kamen et al. |
| 2007/0260421 A1 | 11/2007 | Berner, Jr. et al. |
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0243079 A1* | 10/2008 | Wooley .............. A61M 5/14244 324/426 |
| 2008/0258717 A1 | 10/2008 | Igney et al. |
| 2008/0269673 A1 | 10/2008 | Butoi et al. |
| 2008/0276684 A1 | 11/2008 | Goldbach |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0124988 A1 | 5/2009 | Coulthard |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0209896 A1 | 8/2009 | Selevan |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0191078 A1* | 7/2010 | Yodfat .............. A61M 5/14248 604/131 |
| 2010/0244780 A1 | 9/2010 | Turner et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0208161 A1 | 8/2011 | Ivri |
| 2011/0218384 A1 | 9/2011 | Bachman et al. |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0035562 A1 | 2/2012 | Locke et al. |
| 2012/0109083 A1* | 5/2012 | Coulthard .............. A61F 13/05 604/319 |
| 2012/0112347 A1 | 5/2012 | Eckhardt et al. |
| 2012/0165717 A1 | 6/2012 | Al Khaburi |
| 2012/0190956 A1 | 7/2012 | Connolly |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274563 A1 | 10/2013 | Duesterhoft et al. |
| 2013/0274629 A1 | 10/2013 | Duesterhoft et al. |
| 2013/0317367 A1 | 11/2013 | Shuler |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0174304 A1 | 6/2015 | Askem et al. |
| 2015/0182166 A1 | 7/2015 | Evans et al. |
| 2015/0202353 A1 | 7/2015 | Daughtery |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh et al. |
| 2016/0022223 A1 | 1/2016 | Grundfest et al. |
| 2016/0029900 A1 | 2/2016 | LaPlante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandani et al. |
| 2016/0081580 A1 | 3/2016 | Bergelin et al. |
| 2016/0081601 A1 | 3/2016 | Ballam et al. |
| 2016/0089483 A1 | 3/2016 | Chen |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0165719 A1 | 6/2016 | Li et al. |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi et al. |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331257 A1 | 11/2016 | Baumann et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |
| 2016/0354001 A1 | 12/2016 | Buckley et al. |
| 2016/0367189 A1 | 12/2016 | Aimone et al. |

(56) References Cited

U.S. PATENT DOCUMENTS

| | | |
|---|---|---|
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0086519 A1 | 3/2017 | Vigano' et al. |
| 2017/0086709 A1 | 3/2017 | Khine et al. |
| 2017/0095208 A1 | 4/2017 | Oberleitner et al. |
| 2017/0146474 A1 | 5/2017 | Bedell et al. |
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0319075 A1 | 11/2017 | Homan et al. |
| 2017/0326004 A1 | 11/2017 | Long et al. |
| 2017/0354810 A1 | 12/2017 | O'Brien, III et al. |
| 2017/0367644 A1 | 12/2017 | Sharman et al. |
| 2018/0008177 A1 | 1/2018 | Shimuta et al. |
| 2018/0055359 A1 | 3/2018 | Shamim et al. |
| 2018/0055697 A1 | 3/2018 | Mihali et al. |
| 2018/0056087 A1 | 3/2018 | Ribeiro et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0250458 A1 | 9/2018 | Petersen et al. |
| 2018/0296397 A1 | 10/2018 | Askem et al. |
| 2019/0021911 A1 | 1/2019 | Askem et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0290496 A1 | 9/2019 | Brownhill et al. |
| 2019/0374387 A1 | 12/2019 | Ribble et al. |
| 2020/0054218 A1 | 2/2020 | Xi |
| 2020/0078482 A1 | 3/2020 | Yoon et al. |
| 2020/0078499 A1 | 3/2020 | Gadde et al. |
| 2020/0100711 A1 | 4/2020 | Choudhury et al. |
| 2020/0147407 A1 | 5/2020 | Efremkin |
| 2020/0281512 A1 | 9/2020 | Grubb et al. |
| 2020/0281513 A1 | 9/2020 | Grubb et al. |
| 2020/0281529 A1 | 9/2020 | Grubb et al. |
| 2020/0289346 A1 | 9/2020 | Hansen et al. |
| 2020/0330258 A1 | 10/2020 | Hansen et al. |
| 2020/0360547 A1 | 11/2020 | Smith et al. |
| 2021/0137446 A1 | 5/2021 | Brownhill et al. |
| 2021/0212855 A1 | 7/2021 | Hansen et al. |
| 2022/0079814 A1 | 3/2022 | Chen et al. |

FOREIGN PATENT DOCUMENTS

| | | |
|---|---|---|
| CN | 106102322 A | 11/2016 |
| CN | 109350362 A | 2/2019 |
| DE | 102012211015 A1 | 1/2014 |
| DE | 102013013013 A1 | 2/2015 |
| EP | 2454990 A2 | 5/2012 |
| EP | 2565630 A1 | 3/2013 |
| EP | 2990064 A1 | 3/2016 |
| EP | 3187201 A1 | 7/2017 |
| EP | 3231478 A1 | 10/2017 |
| EP | 3409190 A1 | 12/2018 |
| EP | 3499510 A1 | 6/2019 |
| EP | 3837520 A1 | 6/2021 |
| GB | 1476894 A | 6/1977 |
| GB | 2316171 A | 2/1998 |
| GB | 2563602 A | 12/2018 |
| JP | 2009225863 A | 10/2009 |
| KR | 20120119523 A | 10/2012 |
| KR | 101224629 B1 | 1/2013 |
| KR | 20140024743 A | 3/2014 |
| KR | 20140058041 A | 5/2014 |
| KR | 20160071044 A | 6/2016 |
| KR | 20190105898 A | 9/2019 |
| NL | 1027236 C2 | 4/2006 |
| WO | WO-9632082 A1 | 10/1996 |
| WO | WO-0021433 A1 | 4/2000 |
| WO | WO-0043046 A2 | 7/2000 |
| WO | WO-03067229 A1 | 8/2003 |
| WO | WO-2006041997 A2 | 4/2006 |
| WO | WO-2006122169 A2 | 11/2006 |
| WO | WO-2007030379 A1 | 3/2007 |
| WO | WO-2008006150 A1 | 1/2008 |
| WO | WO-2008010604 A1 | 1/2008 |
| WO | WO-2009052607 A1 | 4/2009 |
| WO | WO-2009120951 A2 | 10/2009 |
| WO | WO-2009141777 A1 | 11/2009 |
| WO | WO-2010020919 A1 | 2/2010 |
| WO | WO-2010105053 A2 | 9/2010 |
| WO | WO-2011082420 A1 | 7/2011 |
| WO | WO-2011123848 A1 | 10/2011 |
| WO | WO-2012141999 A1 | 10/2012 |
| WO | WO-2013026999 A1 | 2/2013 |
| WO | WO-2013044226 A2 | 3/2013 |
| WO | WO-2014036577 A1 | 3/2014 |
| WO | WO-2014116816 A1 | 7/2014 |
| WO | WO-2015112095 A1 | 7/2015 |
| WO | WO-2015168720 A1 | 11/2015 |
| WO | WO-2016025438 A1 | 2/2016 |
| WO | WO-2016030752 A1 | 3/2016 |
| WO | WO-2016058032 A1 | 4/2016 |
| WO | WO-2016073777 A1 | 5/2016 |
| WO | WO-2016100218 A1 | 6/2016 |
| WO | WO-2016109744 A1 | 7/2016 |
| WO | WO-2016110564 A1 | 7/2016 |
| WO | WO-2016187136 A1 | 11/2016 |
| WO | WO-2016205872 A1 | 12/2016 |
| WO | WO-2016205881 A1 | 12/2016 |
| WO | WO-2017021006 A1 | 2/2017 |
| WO | WO-2017021965 A2 | 2/2017 |
| WO | WO-2017033058 A1 | 3/2017 |
| WO | WO-2017037479 A1 | 3/2017 |
| WO | WO-2017041014 A1 | 3/2017 |
| WO | WO-2017041385 A1 | 3/2017 |
| WO | WO-2017041386 A1 | 3/2017 |
| WO | WO-2017041387 A1 | 3/2017 |
| WO | WO-2017119996 A1 | 7/2017 |
| WO | WO-2017205728 A1 | 11/2017 |
| WO | WO-2017214188 A1 | 12/2017 |
| WO | WO-2018035612 A1 | 3/2018 |
| WO | WO-2018060417 A1 | 4/2018 |
| WO | WO-2018064569 A1 | 4/2018 |
| WO | WO-2018115461 A1 | 6/2018 |
| WO | WO-2018144938 A1 | 8/2018 |
| WO | WO-2018144941 A1 | 8/2018 |
| WO | WO-2018144943 A1 | 8/2018 |
| WO | WO-2018144946 A1 | 8/2018 |
| WO | WO-2018185138 A1 | 10/2018 |
| WO | WO-2018189265 A1 | 10/2018 |
| WO | WO-2018209090 A1 | 11/2018 |
| WO | WO-2018210692 A1 | 11/2018 |
| WO | WO-2018211458 A1 | 11/2018 |
| WO | WO-2018234443 A1 | 12/2018 |
| WO | WO-2019020550 A2 | 1/2019 |
| WO | WO-2019020551 A1 | 1/2019 |
| WO | WO-2019020666 A1 | 1/2019 |
| WO | WO-2019030384 A2 | 2/2019 |
| WO | WO-2019048624 A1 | 3/2019 |
| WO | WO-2019048626 A1 | 3/2019 |
| WO | WO-2019048638 A1 | 3/2019 |

(56) References Cited

FOREIGN PATENT DOCUMENTS

| WO | WO-2019063481 A1 | 4/2019 |
| --- | --- | --- |
| WO | WO-2019063488 A2 | 4/2019 |
| WO | WO-2019067264 A1 | 4/2019 |
| WO | WO-2019072531 A1 | 4/2019 |
| WO | WO-2019076967 A2 | 4/2019 |
| WO | WO-2019096828 A1 | 5/2019 |
| WO | WO-2019140441 A2 | 7/2019 |
| WO | WO-2019140444 A1 | 7/2019 |
| WO | WO-2019140448 A1 | 7/2019 |
| WO | WO-2019140449 A1 | 7/2019 |
| WO | WO-2019193141 A1 | 10/2019 |
| WO | WO-2019216883 A1 | 11/2019 |
| WO | WO-2019230183 A1 | 12/2019 |
| WO | WO-2019238180 A1 | 12/2019 |
| WO | WO-2019238181 A1 | 12/2019 |
| WO | WO-2019238182 A1 | 12/2019 |
| WO | WO-2019238195 A1 | 12/2019 |
| WO | WO-2019238196 A1 | 12/2019 |
| WO | WO-2019238197 A1 | 12/2019 |
| WO | WO-2019238198 A1 | 12/2019 |
| WO | WO-2020002416 A1 | 1/2020 |
| WO | WO-2020043806 A1 | 3/2020 |
| WO | WO-2020139541 A1 | 7/2020 |
| WO | WO-2020157103 A1 | 8/2020 |
| WO | WO-2020159677 A1 | 8/2020 |
| WO | WO-2020167547 A1 | 8/2020 |
| WO | WO-2020242876 A1 | 12/2020 |
| WO | WO-2021059209 A1 | 4/2021 |

OTHER PUBLICATIONS

Bandodkar A.J., et al., "Battery-Free, Skin-Interfaced Microfluidic/Electronic Systems for Simultaneous Electrochemical, Colorimetric and Volumetric Analysis of Sweat," Science Advances, vol. 5 (1), Jan. 18, 2019, retrieved from http://advances.sciencemag.org/content/5/1/eaav3294, 16 pages.

Cauwe M., et al., "Technology Development for a Low-Cost, Roll-to-Roll Chip Embedding Solution Based on PET Foils," 18th European Microelectronics and Packaging Conference (EMPC), IEEE, Sep. 12, 2011, 6 pages.

Farooqui M.F., et al., "Low Cost Inkjet Printed Smart Bandage for Wireless Monitoring of Chronic Wounds," Scientific Reports, vol. 6, Jun. 29, 2016, 14 pages.

Geng Y., et al., "A Hybrid Low Power Biopatch for Body Surface Potential Measurement," IEEE Journal of Biomedical and Health Informatics, vol. 17, No. 3, May 1, 2013, pp. 591-599.

George J., et al., "Reliability of Plastic-Encapsulated Electronic Components in Supersaturated Steam Environments," IEEE Transactions on Components, Packaging and Manufacturing Technology, vol. 5 (10), Oct. 2015, pp. 1423-1431.

Iannetta Jr. R.A., et al., "Successful Case Histories of Polymer Based Circuitry on Flexible Film Substrates," Electro/94 International Conference Proceedings Combined Volumes, IEEE, XP010149465, May 10-12, 1994, pp. 885-889.

International Preliminary Report on Patentability for Application No. PCT/EP2019/085271, mailed on Jul. 1, 2021, 9 pages.

International Search Report and Written Opinion for Application No. PCT/EP2019/085271, mailed on Mar. 27, 2020, 12 pages.

Little Miss Plasters, kidstravelclub.co.uk., retrieved from http://www.kidstravelclub.co.uk/little-miss-girls-childrens-plasters on Aug. 26, 2016, 2 pages.

Lu B., et al., "A Study of the Autofluorescence of Parylene Materials for µTAS Applications," Lab on Chip, vol. 10 (14), Jul. 2010, pp. 1826-1834.

McLeod A.J., et al., "Motion Magnification for Endoscopic Surgery," Progress in Biomedical Optics and Imaging, SPIE—International Society for Optical Engineering, Mar. 12, 2014, vol. 9036, 8 pages.

Mehmood N., et al., "Applications of Modern Sensors and Wireless Technology in Effective Wound Management: Modern Sensors And Wireless Technology," Journal of Biomedical Materials Research Part B, vol. 102, May 1, 2014, XP055739544, pp. 885-895.

Mostafalu P., et al., "Wireless Flexible Smart Bandage for Continuous Monitoring of Wound Oxygenation," IEEE Transactions on Biomedical Circuits and Systems, vol. 9 (5), Oct. 1, 2015, XP055526132, pp. 670-677 (8 pages).

Narusawa H., "The Corona Discharge Causes Short Destruction that had Bad Influence on a Power Switching Circuit," Adphox Corporation, Jan. 1, 2009, retrieved from http://www.adphox.co.jp/keisokuki/ke-english-corona/CORONA_DISCHARGE_EN.pdf, 12 pages.

Raviglione A., et al., "Real-Time Smart Textile-Based System to Monitor Pressure Offloading of Diabetic Foot Ulcers," Journal of Diabetes Science and Technology, vol. 11 (5), Sep. 2017, pp. 894-898.

Rose D.P., et al., "Adhesive RFID Sensor Patch for Monitoring of Sweat Electrolytes," IEEE Transactions on Biomedical Engineering, vol. 62 (6), Jun. 2015, first published on Nov. 11, 2015, pp. 1457-1465.

Wakita J., et al., "Variations in Optical Absorption and Fluorescence Spectra for Polyimide Thin Films Caused by Structural Isomerism," Journal of Photopolymer Science and Technology, Jan. 1, 2003, 1 page.

Willis B., "Conformal Coating Inspection & Coating Faults," Vision Engineering, Jul. 21, 2016, retrieved from http://www.visioneng.com/wp-content/uploads/2017/11/Conformal-Coating-Inspection-and-Defects.21JUL16.pdf, 35 pages.

Willis B., "Guide to Conformal Coating & Cleaning Defects Contents," Mar. 1, 2014, retrieved from http://coatingguide.smartgroup.org/Files%20pdf/Coating%20Defects%20V2%2014March2014.pdf, vol. 1, 31 pages.

\* cited by examiner

WOUND THERAPY SYSTEMS AND METHODS WITH MULTIPLE POWER SOURCES

CROSS-REFERENCE TO RELATED APPLICATIONS

This application is a continuation of U.S. application Ser. No. 17/414,729, filed on Jun. 16, 2021, which is a U.S. national phase of International Patent Application No. PCT/EP2019/085271, filed on Dec. 16, 2019, which claims priority to U.K. Provisional Application No. 1820927.0, filed on Dec. 21, 2018, entitled "WOUND THERAPY SYSTEMS AND METHODS WITH SUPERCAPACITORS," the disclosure of each of which is hereby incorporated by reference in its entirety.

FIELD

Embodiments of the present disclosure relate to apparatuses, systems, and methods for the treatment of tissues via sensor-enabled monitoring in communication with various therapy regimes.

BACKGROUND

Nearly all areas of medicine may benefit from improved information regarding the state of the tissue, organ, or system to be treated, particularly if such information is gathered in real-time during treatment. Many types of treatments are still routinely performed without the use of sensor data collection; instead, such treatments rely upon visual inspection by a caregiver or other limited means rather than quantitative sensor data. For example, in the case of wound treatment via dressings or negative pressure wound therapy, data collection is generally limited to visual inspection by a caregiver and often the underlying wounded tissue may be obscured by bandages or other visual impediments. Even intact, unwounded skin may have underlying damage that is not visible to the naked eye, such as a compromised vascular or deeper tissue damage that may lead to an ulcer. Similar to wound treatment, during orthopedic treatments requiring the immobilization of a limb with a cast or other encasement, only limited information is gathered on the underlying tissue. In instances of internal tissue repair, such as a bone plate, continued direct sensor-driven data collection is not performed. Further, braces or sleeves used to support musculoskeletal function do not monitor the functions of the underlying muscles or the movement of the limbs. Outside of direct treatments, common hospital room items such as beds and blankets could be improved by adding capability to monitor patient parameters.

Therefore, there is a need for improved sensor monitoring, particularly through the use of sensor-enabled substrates which can be incorporated into existing treatment regimes.

SUMMARY

Some embodiments of the present disclosure provide an improved system for providing therapy to a wound. A system for providing therapy to a wound can include a pressure source. The pressure source can be configured to provide negative pressure to a wound dressing positioned over a wound. The system can further include one or more controllers. The one or more controller can be configured to operate the pressure source and communicate with a first electronic component. The system can further include a first power source configured to power the first electronic component. The first power source can include a battery. The system can further include a second power source configured to power the first electronic component in place of the first power source. The second power source can include a capacitor.

The system of the preceding paragraph may also include any combination of the following features described in this paragraph, among other features described herein. The one or more controllers can be configured to, responsive to a first condition, cause the capacitor to power the first electronic component in place of the battery. The battery can be configured to power a second electronic component. The one or more controllers can be configured to, responsive to the first condition, cause the capacitor to power the first electronic component in place of the battery without causing the capacitor to power the second electronic component in place of the battery. The one or more controllers can be configured to, responsive to a second condition, cause the battery to power to the first electronic component in place of the capacitor. At least one of the first condition or the second condition can correspond to a capacity of the battery or the capacitor. The one or more controllers can be configured to determine an occurrence of the first condition or the second condition from a comparison of a value to a threshold, the value being indicative of a capacity of the battery or a capacity of the capacitor.

The system of any of the preceding paragraphs may also include any combination of the following features described in this paragraph, among other features described herein. At least one of the first electronic component or the second electronic component can include a clock or a wireless communications device. The first electronic component can include a sensor. The sensor can be configured to be positioned proximate the wound and provide measurement data to the one or more controllers. The measurement data can be usable by the one or more controllers to monitor healing of the wound.

The system of any of the preceding paragraphs may also include any combination of the following features described in this paragraph, among other features described herein. The first electronic component can include an electrical stimulator. The first electronic component can be supported by the wound dressing. The pressure source, the one or more controllers, the capacitor, and the battery are supported by the wound dressing. The capacitor can have a capacitance of between 100 mF to 100 F, 1 F to 10 F, or 2 F to 5 F. The one or more controllers can be a single controller. The capacitor can be configured to be charged by a power source other than the battery. The power source can be a coin cell. The battery can be configured to power the pressure source or the one or more controllers. A method of using the system of this paragraph or any of the preceding paragraphs can be provided.

Some embodiments of the present disclosure provide an improved wound monitoring or therapy apparatus. A wound monitoring or therapy apparatus can include a controller configured to communicate with a first electronic component. The wound monitoring or therapy apparatus can also include a first and second power source. The first power source can include a battery configured to power the first electronic component. The second power source can include a capacitor configured to power to the first electronic component in place of the battery.

The wound monitoring or therapy apparatus of the preceding paragraph may also include any combination of the following features described in this paragraph, among other features described herein. The controller can be configured to, responsive to a first condition, cause the capacitor to power the first electronic component in place of the battery. The battery can be configured to power a second electronic component. The controller can be configured to, responsive to the first condition, cause the capacitor to power the first electronic component in place of the battery without causing the capacitor to power the second electronic component in place of the battery. The controller can be configured to, responsive to a second condition, cause the battery to power to the first electronic component in place of the capacitor. The first condition or the second condition can be indicative of a capacity of the battery or a capacity of the capacitor. The controller can be configured to determine an occurrence of the first condition or the second condition from a comparison of a value to a threshold. The value can be indicative of a capacity of the battery or a capacity of the capacitor.

The wound monitoring or therapy apparatus of any of the preceding paragraphs may also include any combination of the following features described in this paragraph, among other features described herein. The first electronic component can include a clock or a wireless communications device. The first electronic component can include a sensor. The sensor can be configured to be positioned proximate a wound and provide measurement data to the controller, the measurement data being usable by the controller to monitor healing of the wound. The first electronic component can include an electrical stimulator. The capacitor can have a capacitance value of between 100 mF to 100 F, 1 F to 10 F, or 2 F to 5 F. The controller can be a single controller. The controller can include a plurality of controllers. The capacitor can be configured to be charged by a power source other than the battery.

The wound monitoring or therapy apparatus of any of the preceding paragraphs may also include any combination of the following features described in this paragraph, among other features described herein. The capacitor can be configured to be charged by a coin cell. The capacitor can be configured to be charged by the battery. The battery can be configured to power the pressure source or the controller. The capacitor can be configured to power the pressure source or the controller. The wound monitoring or therapy apparatus can further include a wound dressing configured to be positioned in contact with a wound. The first electronic component can be supported by the wound dressing. The battery or the capacitor can be supported by the wound dressing. The controller can be supported by the wound dressing. The system can further include a negative pressure source configured to provide negative pressure to the wound dressing. A method of using the wound monitoring or therapy apparatus of this paragraph or any of the preceding paragraphs can be provided.

Any of the features, components, or details of any of the arrangements or embodiments disclosed in this application, including without limitation any of the pump embodiments, any of the negative pressure wound therapy embodiments, any of the wound dressing embodiments, or any of the optical sensor embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which.

DETAILED DESCRIPTION

Figure 1A:
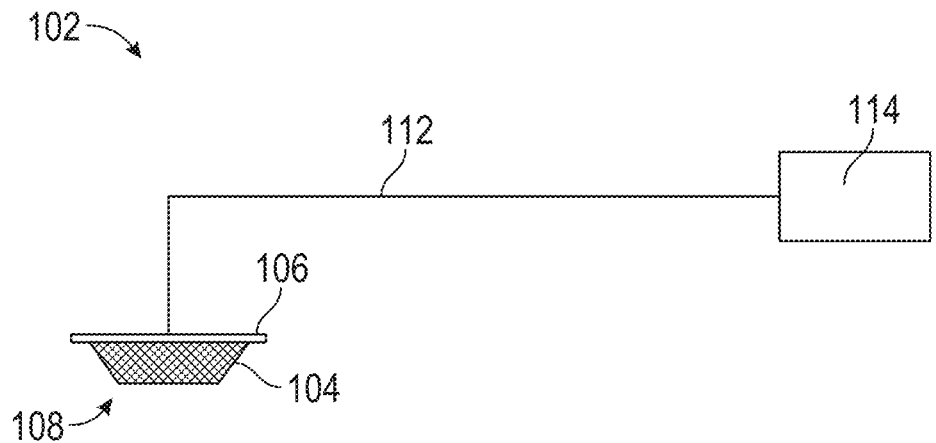
FIG. 1A illustrates an example negative pressure wound treatment system.

Examples disclosed herein relate to apparatuses and methods of monitoring and treating biological tissue with sensor-enabled substrates. The examples disclosed herein are not limited to treatment or monitoring of a particular type of tissue or injury, instead the sensor-enabled technologies disclosed herein are broadly applicable to any type of therapy that may benefit from sensor-enabled substrates. Some implementations utilize sensors and data collection relied upon by health care providers to make both diagnostic and patient management decisions.

Some examples disclosed herein relate to the use of sensors mounted on or embedded within substrates configured to be used in the treatment of both intact and damaged human or animal tissue. Such sensors may collect information about the surrounding tissue and transmit such information to a computing device or a caregiver to be utilized in further treatment. In certain examples, such sensors may be attached to the skin anywhere on the body, including areas for monitoring arthritis, temperature, or other areas that may be prone to problems and require monitoring. Sensors disclosed herein may also incorporate markers, such as radiopaque markers, to indicate the presence of the device, for example prior to performing an MRI or other technique.

The sensor examples disclosed herein may be used in combination with clothing. Non-limiting examples of clothing for use with the sensors disclosed herein include shirts, pants, trousers, dresses, undergarments, outer-garments, gloves, shoes, hats, and other suitable garments. In certain examples, the sensor examples disclosed herein may be welded into or laminated into/onto the particular garments. The sensor examples may be printed directly onto the garment or embedded into the fabric. Breathable and printable materials such as microporous membranes may also be suitable.

Sensor examples disclosed herein may be incorporated into cushioning or bed padding, such as within a hospital bed, to monitor patient characteristics, such as any characteristic disclosed herein. In certain examples, a disposable film containing such sensors could be placed over the hospital bedding and removed/replaced as needed.

In some implementations, the sensor examples disclosed herein may incorporate energy harvesting, such that the sensor examples are self-sustaining. For example, energy may be harvested from thermal energy sources, kinetic energy sources, chemical gradients, or any suitable energy source.

The sensor examples disclosed herein may be utilized in rehabilitation devices and treatments, including sports medicine. For example, the sensor examples disclosed herein may be used in braces, sleeves, wraps, supports, and other suitable items. Similarly, the sensor examples disclosed herein may be incorporated into sporting equipment, such as helmets, sleeves, or pads. For example, such sensor examples may be incorporated into a protective helmet to monitor characteristics such as acceleration, which may be useful in concussion diagnosis.

The sensor examples disclosed herein may be used in coordination with surgical devices, for example, the NAVIO surgical system by Smith & Nephew Inc. In implementations, the sensor examples disclosed herein may be in communication with such surgical devices to guide placement of the surgical devices. In some implementations, the sensor examples disclosed herein may monitor blood flow to or away from the potential surgical site or ensure that there is no blood flow to a surgical site. Further surgical data may be collected to aid in the prevention of scarring and monitor areas away from the impacted area.

To further aid in surgical techniques, the sensors disclosed herein may be incorporated into a surgical drape to provide information regarding tissue under the drape that may not be immediately visible to the naked eye. For example, a sensor embedded flexible drape may have sensors positioned advantageously to provide improved area-focused data collection. In certain implementations, the sensor examples disclosed herein may be incorporated into the border or interior of a drape to create fencing to limit/control the surgical theater.

Sensor examples as disclosed herein may also be utilized for pre-surgical assessment. For example, such sensor examples may be used to collect information about a potential surgical site, such as by monitoring skin and the underlying tissues for a possible incision site. For example, perfusion levels or other suitable characteristics may be monitored at the surface of the skin and deeper in the tissue to assess whether an individual patient may be at risk for surgical complications. Sensor examples such as those disclosed herein may be used to evaluate the presence of microbial infection and provide an indication for the use of antimicrobials. Further, sensor examples disclosed herein may collect further information in deeper tissue, such as identifying pressure ulcer damage or the fatty tissue levels.

The sensor examples disclosed herein may be utilized in cardiovascular monitoring. For example, such sensor examples may be incorporated into a flexible cardiovascular monitor that may be placed against the skin to monitor characteristics of the cardiovascular system and communicate such information to another device or a caregiver. For example, such a device may monitor pulse rate, oxygenation of the blood, or electrical activity of the heart. Similarly, the sensor examples disclosed herein may be utilized for neurophysiological applications, such as monitoring electrical activity of neurons.

The sensor examples disclosed herein may be incorporated into implantable devices, such as implantable orthopedic implants, including flexible implants. Such sensor examples may be configured to collect information regarding the implant site and transmit this information to an external source. In some cases, an internal source may also provide power for such an implant.

The sensor examples disclosed herein may also be utilized for monitoring biochemical activity on the surface of the skin or below the surface of the skin, such as lactose buildup in muscle or sweat production on the surface of the skin. In some cases, other characteristics may be monitored, such as glucose concentration, urine concentration, tissue pressure, skin temperature, skin surface conductivity, skin surface resistivity, skin hydration, skin maceration, or skin ripping.

Sensor examples as disclosed herein may be incorporated into Ear, Nose, and Throat (ENT) applications. For example, such sensor examples may be utilized to monitor recovery from ENT-related surgery, such as wound monitoring within the sinus passage.

As described in greater detail below, the sensor examples disclosed herein may encompass sensor printing technology with encapsulation, such as encapsulation with a polymer film. Such a film may be constructed using any polymer described herein, such as polyurethane. Encapsulation of the sensor examples may provide waterproofing of the electronics and protection from local tissue, local fluids, and other sources of potential damage.

In certain examples, the sensors disclosed herein may be incorporated into an organ protection layer such as disclosed below. Such a sensor-embedded organ protection layer may both protect the organ of interest and confirm that the organ protection layer is in position and providing protection. Further, a sensor-embedded organ protection layer may be utilized to monitor the underlying organ, such as by monitoring blood flow, oxygenation, and other suitable markers of organ health. In some cases, a sensor-enabled organ protection layer may be used to monitor a transplanted organ, such as by monitoring the fat and muscle content of the organ. Further, sensor-enabled organ protection layers may be used to monitor an organ during and after transplant, such as during rehabilitation of the organ.

The sensor examples disclosed herein may be incorporated into treatments for wounds (disclosed in greater detail below) or in a variety of other applications. Non-limiting examples of additional applications for the sensor examples disclosed herein include: monitoring and treatment of intact skin, cardiovascular applications such as monitoring blood flow, orthopedic applications such as monitoring limb movement and bone repair, neurophysiological applications such as monitoring electrical impulses, and any other tissue, organ, system, or condition that may benefit from improved sensor-enabled monitoring.

Wound Therapy

Some examples disclosed herein relate to wound therapy for a human or animal body. Therefore, any reference to a wound herein can refer to a wound on a human or animal body, and any reference to a body herein can refer to a human or animal body. The disclosed technology examples may relate to preventing or minimizing damage to physiological tissue or living tissue, or to the treatment of damaged tissue (for example, a wound as described herein) wound with or without reduced pressure, including for example a source of negative pressure and wound dressing components and apparatuses. The apparatuses and components comprising the wound overlay and packing materials or internal layers, if any, are sometimes collectively referred to herein as dressings. In some cases, the wound dressing can be provided to be utilized without reduced pressure.

Some examples disclosed herein relate to wound therapy for a human or animal body. Therefore, any reference to a wound herein can refer to a wound on a human or animal body, and any reference to a body herein can refer to a human or animal body. The disclosed technology examples may relate to preventing or minimizing damage to physiological tissue or living tissue, or to the treatment of damaged tissue (for example, a wound as described herein).

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some examples relate to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure or traditional advanced wound care, which is not aided by the using of applied negative pressure (may also be referred to as non-negative pressure therapy).

Advanced wound care may include use of an absorbent dressing, an occlusive dressing, use of an antimicrobial or debriding agents in a wound dressing or adjunct, a pad (for example, a cushioning or compressive therapy, such as stockings or bandages), or the like.

In some cases, treatment of such wounds can be performed using traditional wound care, wherein a dressing can be applied to the wound to facilitate and promote healing of the wound.

Some examples relate to methods of manufacturing a wound dressing comprising providing a wound dressing as disclosed herein.

Negative Pressure Wound Dressing

In some cases, treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that examples of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy (NPWT) involves placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria.

Some of the dressings used in NPWT can include many different types of materials and layers, for example, gauze, pads, foam pads or multi-layer wound dressings. One example of a multi-layer wound dressing is the PICO dressing, available from Smith & Nephew, includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (such as, −40 mmHg is less than −60 mmHg). Negative pressure that is "more" or "greater" than −X mmHg corresponds to pressure that is further from atmospheric pressure (such as, −80 mmHg is more than −60 mmHg). In some cases, local ambient atmospheric pressure is used as a reference point, and such local atmospheric pressure may not necessarily be, for example, 760 mmHg.

The negative pressure range for some examples of the present disclosure can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some cases, the pressure range can be between about −40 mmHg and −150 mmHg. Alternatively, a pressure range of up to −75 mmHg, up to −80 mmHg or over −80 mmHg can be used. Also in other examples, a pressure range of below −75 mmHg can be used. Alternatively, a pressure range of over approximately −100 mmHg, or even −150 mmHg, can be supplied by the negative pressure apparatus.

In some examples of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via examples of the wound closure devices. In some cases, negative pressure may be varied over time for example using a sinusoidal wave, square wave, or in synchronization with one or more patient physiological indices (such as, heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Examples of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,908, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Examples of the wound dressings, wound dressing assembly, wound dressing components, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158 A1 on Nov. 24, 2016, titled "FLUIDIC CONNECTOR FOR NEGATIVE PRESSURE WOUND THERAPY," the disclosure of each of which is hereby incorporated by reference in its entirety, including further details relating to examples of wound dressings, the wound dressing components and principles, and the materials used for the wound dressings.

Additionally, some examples related to TNP wound treatment comprising a wound dressing in combination with a pump or associated electronics described herein may also be used in combination or in addition to those described in International Application PCT/EP2016/059329 filed Apr. 26, 2016, published as WO 2016/174048 on Nov. 3, 2016, entitled "REDUCED PRESSURE APPARATUS AND METHODS," the disclosure of which is hereby incorporated by reference in its entirety.

NPWT System Overview

FIG. 1A illustrates an example of a negative or reduced pressure wound treatment (or TNP) system 102 comprising a wound filler 108 placed inside a wound cavity 104, the wound cavity sealed by a wound cover 106. The wound filler 108 in combination with the wound cover 106 can be referred to as wound dressing. A single or multi lumen tube or conduit 112 is connected the wound cover 106 with a pump assembly 114 configured to supply reduced pressure. The wound cover 106 can be in fluidic communication with the wound cavity 104. In any of the system examples disclosed herein, as in the example illustrated in FIG. 1A, the pump assembly can be a canisterless pump assembly (meaning that exudate is collected in the wound dressing or is transferred via tube 112 for collection to another location). However, any of the pump assembly examples disclosed herein can be configured to include or support a canister. Additionally, in any of the system examples disclosed herein, any of the pump assembly examples can be mounted to or supported by the dressing, or adjacent to the dressing.

The wound filler 108 can be any suitable type, such as hydrophilic or hydrophobic foam, gauze, inflatable bag, and so on. The wound filler 108 can be conformable to the wound cavity 104 such that it substantially fills the cavity. The wound cover 106 can provide a substantially fluid impermeable seal over the wound cavity 104. The wound cover 106 can have a top side and a bottom side, and the bottom side adhesively (or in any other suitable manner) seals with wound cavity 104. The conduit 112 or lumen or any other conduit or lumen disclosed herein can be formed from polyurethane, PVC, nylon, polyethylene, silicone, or any other suitable material.

Some examples of the wound cover 106 can have a port (not shown) configured to receive an end of the conduit 112. For example, the port can be Renays Soft Port available from Smith & Nephew. In other cases, the conduit 112 can otherwise pass through or under the wound cover 106 to supply reduced pressure to the wound cavity 104 so as to maintain a desired level of reduced pressure in the wound cavity. The conduit 112 can be any suitable article configured to provide at least a substantially sealed fluid flow pathway between the pump assembly 114 and the wound cover 106, so as to supply the reduced pressure provided by the pump assembly 114 to wound cavity 104.

The wound cover 106 and the wound filler 108 can be provided as a single article or an integrated single unit. In some cases, no wound filler is provided and the wound cover by itself may be considered the wound dressing. The wound dressing may then be connected, via the conduit 112, to a source of negative pressure, such as the pump assembly 114. The pump assembly 114 can be miniaturized and portable, although larger conventional pumps such can also be used.

The wound cover 106 can be located over a wound site to be treated. The wound cover 106 can form a substantially sealed cavity or enclosure over the wound site. In some cases, the wound cover 106 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some examples of the system are designed to operate without the use of an exudate canister. Some examples can be configured to support an exudate canister. In some cases, configuring the pump assembly 114 and tubing 112 so that the tubing 112 can be quickly and easily removed from the pump assembly 114 can facilitate or improve the process of dressing or pump changes, if necessary. Any of the pump examples disclosed herein can be configured to have any suitable connection between the tubing and the pump.

The pump assembly 114 can be configured to deliver negative pressure of approximately −80 mmHg, or between about −20 mmHg and −200 mmHg in some implementations. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even −150 mmHg, can be supplied by the pump assembly 114.

In operation, the wound filler 108 is inserted into the wound cavity 104 and wound cover 106 is placed so as to seal the wound cavity 104. The pump assembly 114 provides a source of a negative pressure to the wound cover 106, which is transmitted to the wound cavity 104 via the wound filler 108. Fluid (such as, wound exudate) is drawn through the conduit 112, and can be stored in a canister. In some cases, fluid is absorbed by the wound filler 108 or one or more absorbent layers (not shown).

Wound dressings that may be utilized with the pump assembly and other examples of the present application include Renasys-F, Renasys-G, Renasys AB, and Pico Dressings available from Smith & Nephew. Further description of such wound dressings and other components of a negative pressure wound therapy system that may be used with the pump assembly and other examples of the present application are found in U.S. Patent Publication Nos. 2011/0213287, 2011/0282309, 2012/0116334, 2012/0136325, and 2013/0110058, which are incorporated by reference in their entirety. In other examples, other suitable wound dressings can be utilized.

Wound Dressing Overview

Figure 1B:
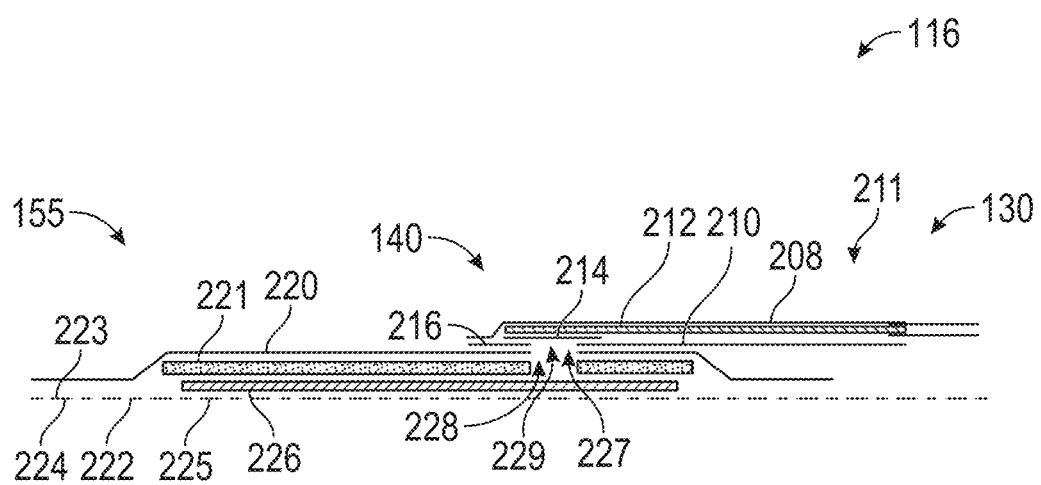
FIG. 1B illustrates an example wound dressing.

FIG. 1B illustrates an example cross-section through a wound dressing 155. FIG. 1B also illustrates an example fluidic connector 116. The wound dressing 155 can be similar to the wound dressing described in International Patent Publication WO2013175306 A2, which is incorporated by reference in its entirety. Alternatively, the wound dressing 155 can be any wound dressing example disclosed herein or any combination of features of any number of wound dressing examples disclosed herein, can be located over a wound site to be treated. The wound dressing 155 may be placed as to form a sealed cavity over the wound, such as the wound cavity 104. In some cases, the wound dressing 155 includes a top or cover layer, or backing layer 220 attached to an optional wound contact layer 222, both of which are described in greater detail below. These two layers 220, 222 can be joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

The wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 (for example, facing the wound) and an upper surface 223 (for example, facing away from the wound). The perforations 225 can comprise through holes in the wound contact layer 222 which enable fluid to flow through the layer 222. The wound contact layer 222 helps prevent tissue ingrowth into the other material of the wound dressing. In some cases, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 155 while also creating an air tight seal around the absorbent pad in order to maintain negative pressure at the wound. In some cases, the wound contact layer is configured to allow unidirectional or substantially one-way or unidirectional flow of fluid through the wound contact layer when negative pressure is applied to the wound. For example, the wound contact layer can permit fluid to flow away from the wound through the wound contact layer, but not allow fluid to flow back toward the wound. In certain case, the perforations in the wound contact layer are configured to permit such one-way or unidirectional flow of fluid through the wound contact layer.

Some examples of the wound contact layer 222 may also act as a carrier for an optional lower and upper adhesive layer (not shown). For example, a lower pressure sensitive adhesive may be provided on the lower surface 224 of the wound dressing 155 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 155 to the skin around a wound site. In some cases, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some cases, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In particular, the transmission layer 226 can ensure that an open air channel can be maintained to communicate negative pressure over the wound area even when the absorbent layer has absorbed substantial amounts of exudates. The layer 226 can remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some cases, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

In some cases, to improve the liquid flow across the transmission layer 226 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats or waxes used previously which might interfere with the hydrophilic capabilities of the transmission layer. An additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material can be provided above the transmission layer 226. The absorbent material, which comprise a foam or non-woven natural or synthetic material, and which may optionally comprise a super-absorbent material, forms a reservoir for fluid, particularly liquid, removed from the wound site. In some cases, the layer 221 may also aid in drawing fluids towards the backing layer 220.

The material of the absorbent layer 221 may also prevent liquid collected in the wound dressing 155 from flowing freely within the dressing, and can act so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 or Chem-Posite™11C-450. In some cases, the absorbent layer 221 may comprise a composite comprising superabsorbent powder, fibrous material such as cellulose, and bonding fibers. In some cases, the composite is an airlaid, thermally-bonded composite.

In some cases, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 can be provided in the backing layer 220 to allow a negative pressure to be applied to the dressing 155. In some cases, the fluidic connector 116 is attached or sealed to the top of the backing layer 220 over the orifice 227 made into the dressing 155, and communicates negative pressure through the orifice 227. A length of tubing may be coupled at a first end to the fluidic connector 116 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 116 may be adhered and sealed to the backing layer 220 using an adhesive such as an acrylic, cyanoacrylate, epoxy, UV curable or hot melt adhesive. The fluidic connector 116 may be formed from a soft polymer, for example a polyethylene, a polyvinyl chloride, a silicone or polyurethane having a hardness of 30 to 90 on the Shore A scale. In some cases, the fluidic connector 116 may be made from a soft or conformable material.

In some cases, the absorbent layer 221 includes at least one through hole 228 located so as to underlie the fluidic connector 116. The through hole 228 may in some cases be the same size as the opening 227 in the backing layer, or may be bigger or smaller. As illustrated in FIG. 1B a single through hole can be used to produce an opening underlying the fluidic connector 116. It will be appreciated that multiple openings could alternatively be utilized. Additionally should more than one port be utilized according to certain examples of the present disclosure one or multiple openings may be made in the absorbent layer and the obscuring layer in registration with each respective fluidic connector. Although not essential to certain examples of the present disclosure the use of through holes in the super-absorbent layer may provide a fluid flow pathway which remains unblocked in particular when the absorbent layer is near saturation.

The aperture or through-hole 228 can be provided in the absorbent layer 221 beneath the orifice 227 such that the orifice is connected directly to the transmission layer 226 as illustrated in FIG. 1B. This allows the negative pressure applied to the fluidic connector 116 to be communicated to the transmission layer 226 without passing through the absorbent layer 221. This ensures that the negative pressure applied to the wound site is not inhibited by the absorbent layer as it absorbs wound exudates. In other cases, no aperture may be provided in the absorbent layer 221, or alternatively a plurality of apertures underlying the orifice 227 may be provided. In further alternative examples, additional layers such as another transmission layer or an obscuring layer such as described in International Patent Publication WO2014020440, the entirety of which is hereby incorporated by reference, may be provided over the absorbent layer 221 and beneath the backing layer 220.

The backing layer 220 is can be gas impermeable, but moisture vapor permeable, and can extend across the width of the wound dressing 155. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 220 and a wound site where a negative pressure can be established. The backing layer 220 can be sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 can include two layers; a polyurethane film and an adhesive pattern spread onto the film. The polyurethane film can be moisture vapor permeable and may be manufactured from a material that has an increased water transmission rate when wet. In some cases, the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIG. 1B, the absorbent layer 221 may define a smaller perimeter than that of the backing layer 220, such that a boundary or border region is defined between the edge of the absorbent layer 221 and the edge of the backing layer 220.

As shown in FIG. 1B, one example of the wound dressing 155 comprises an aperture 228 in the absorbent layer 221 situated underneath the fluidic connector 116. In use, for example when negative pressure is applied to the dressing 155, a wound facing portion of the fluidic connector may thus come into contact with the transmission layer 226, which can thus aid in transmitting negative pressure to the wound site even when the absorbent layer 221 is filled with wound fluids. Some examples may have the backing layer 220 be at least partly adhered to the transmission layer 226. In some cases, the aperture 228 is at least 1-2 mm larger than the diameter of the wound facing portion of the fluidic connector 11, or the orifice 227.

For example, in examples with a single fluidic connector 116 and through hole, it may be preferable for the fluidic connector 116 and through hole to be located in an off-center position. Such a location may permit the dressing 155 to be positioned onto a patient such that the fluidic connector 116 is raised in relation to the remainder of the dressing 155. So positioned, the fluidic connector 116 and the filter 214 may be less likely to come into contact with wound fluids that could prematurely occlude the filter 214 so as to impair the transmission of negative pressure to the wound site.

Turning now to the fluidic connector 116, some examples include a sealing surface 216, a bridge 211 with a proximal end (closer to the negative pressure source) and a distal end 140, and a filter 214. The sealing surface 216 can form the applicator that is sealed to the top surface of the wound dressing. In some cases, a bottom layer of the fluidic connector 116 may comprise the sealing surface 216. The fluidic connector 116 may further comprise an upper surface vertically spaced from the sealing surface 216, which in some examples is defined by a separate upper layer of the fluidic connector. In other cases, the upper surface and the lower surface may be formed from the same piece of material. In some cases, the sealing surface 216 may comprise at least one aperture 229 therein to communicate with the wound dressing. In some cases, the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some cases, the sealing surface 216 may be placed over an orifice in the cover layer with optional spacer elements 215 configured to create a gap between the filter 214 and the transmission layer 226. In other cases, the sealing surface 216 may be positioned over an orifice in the cover layer and an aperture in the absorbent layer 220, permitting the fluidic connector 116 to provide air flow through the transmission layer 226. In some cases, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 can be encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge, and spacer elements 215 are configured to prevent the fluidic connector from contacting the transmission layer 226. These elements will be described in greater detail below.

Some examples may further comprise an optional second fluid passage positioned above the first fluid passage 212. For example, some examples may provide for an air leak may be disposed at the proximal end of the top layer that is configured to provide an air path into the first fluid passage 212 and dressing 155 similar to the suction adapter as described in U.S. Pat. No. 8,801,685, which is incorporated by reference herein in its entirety.

In some cases, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some cases, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some cases, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected can be suited to channeling wound exudate away from the wound and for transmitting negative pressure or vented air to the wound site, and may also confer a degree of kinking or occlusion resistance to the fluid passage 212. In some cases, the wicking fabric may have a three-dimensional structure, which in some cases may aid in wicking fluid or transmitting negative pressure. In certain examples, including wicking fabrics, these materials remain open and capable of communicating negative pressure to a wound area under the typical pressures used in negative pressure therapy, for example between −40 to −150 mmHg. In some cases, the wicking fabric may comprise several layers of material stacked or layered over each other, which may in some cases be useful in preventing the fluid passage 212 from collapsing under the application of negative pressure. In other cases, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other cases, the fluid passage 212 may be between 1.2-3 mm thick, and preferably thicker than 1.5 mm. Some examples, for example a suction adapter used with a dressing which retains liquid such as wound exudate, may employ hydrophobic layers in the fluid passage 212, and only gases may travel through the fluid passage 212. Additionally, and as described previously, the materials used in the system can be conformable and soft, which may help to avoid pressure ulcers and other complications which may result from a wound treatment system being pressed against the skin of a patient.

In some cases, the filter element 214 is impermeable to liquids, but permeable to gases, and is provided to act as a liquid barrier and to ensure that no liquids are able to escape from the wound dressing 155. The filter element 214 may also function as a bacterial barrier. Typically the pore size is 0.2 μm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port or the cover film over the orifice. For example, the filter element 214 may be molded into the fluidic connector 116, or may be adhered to one or both of the top of the cover layer and bottom of the suction adapter 160 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some cases, filter element 214 comprises a support layer and an acrylic co-polymer membrane formed on the support layer. In some cases, the wound dressing 155 according to certain examples uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

The wound dressing 155 may comprise spacer elements 215 in conjunction with the fluidic connector 116 and the filter 214. With the addition of such spacer elements 215 the fluidic connector 116 and filter 214 may be supported out of direct contact with the absorbent layer 220 or the transmission layer 226. The absorbent layer 220 may also act as an additional spacer element to keep the filter 214 from contacting the transmission layer 226. Accordingly, with such a configuration contact of the filter 214 with the transmission layer 226 and wound fluids during use may thus be minimized.

Similar to the examples of wound dressings described above, some wound dressings comprise a perforated wound contact layer with silicone adhesive on the skin-contact face and acrylic adhesive on the reverse. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

Figure 1C:
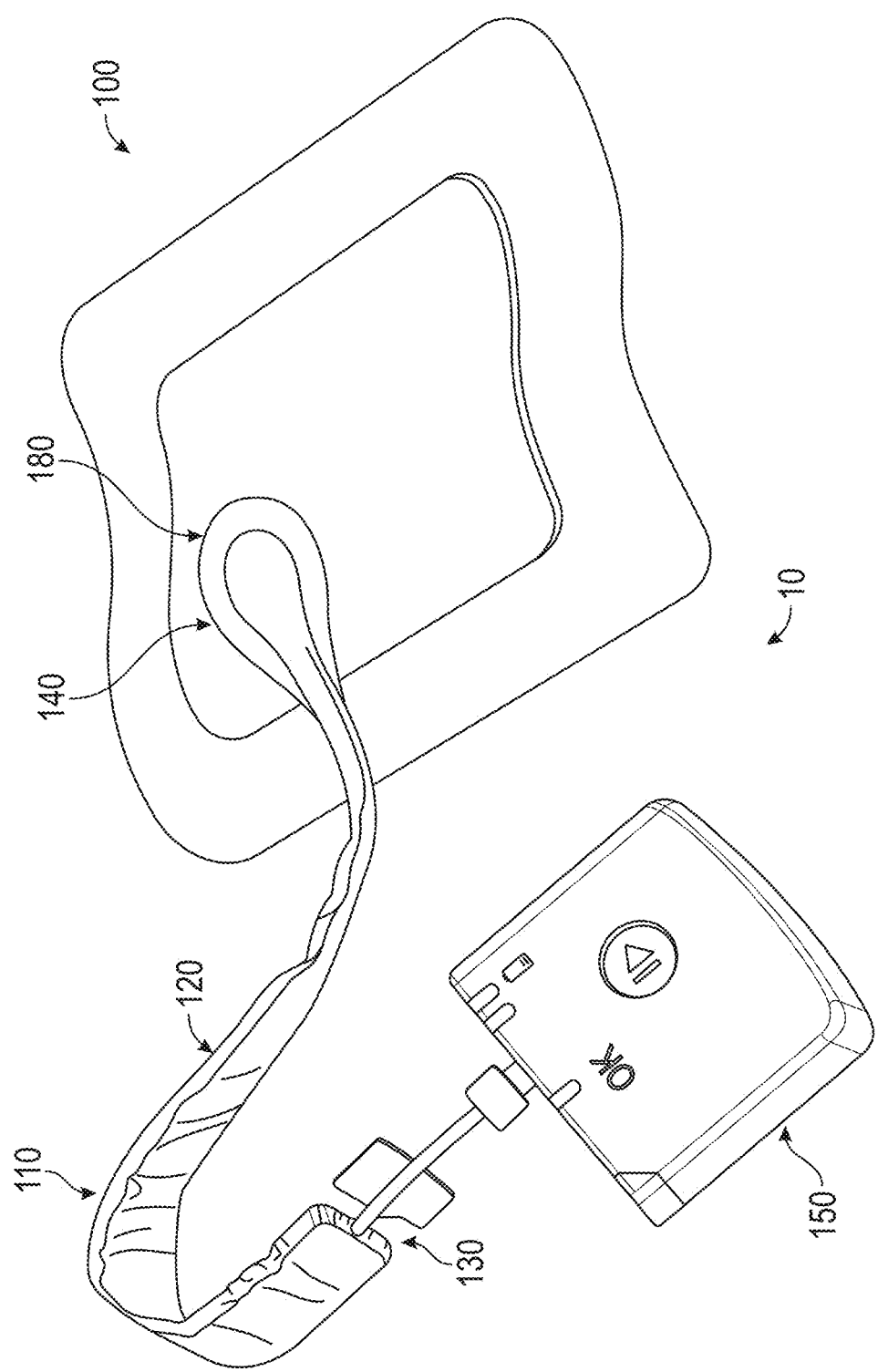
FIG. 1C illustrates an example negative pressure wound treatment system employing a flexible fluidic connector and a wound dressing capable of absorbing and storing wound exudate.
Figure 1D:
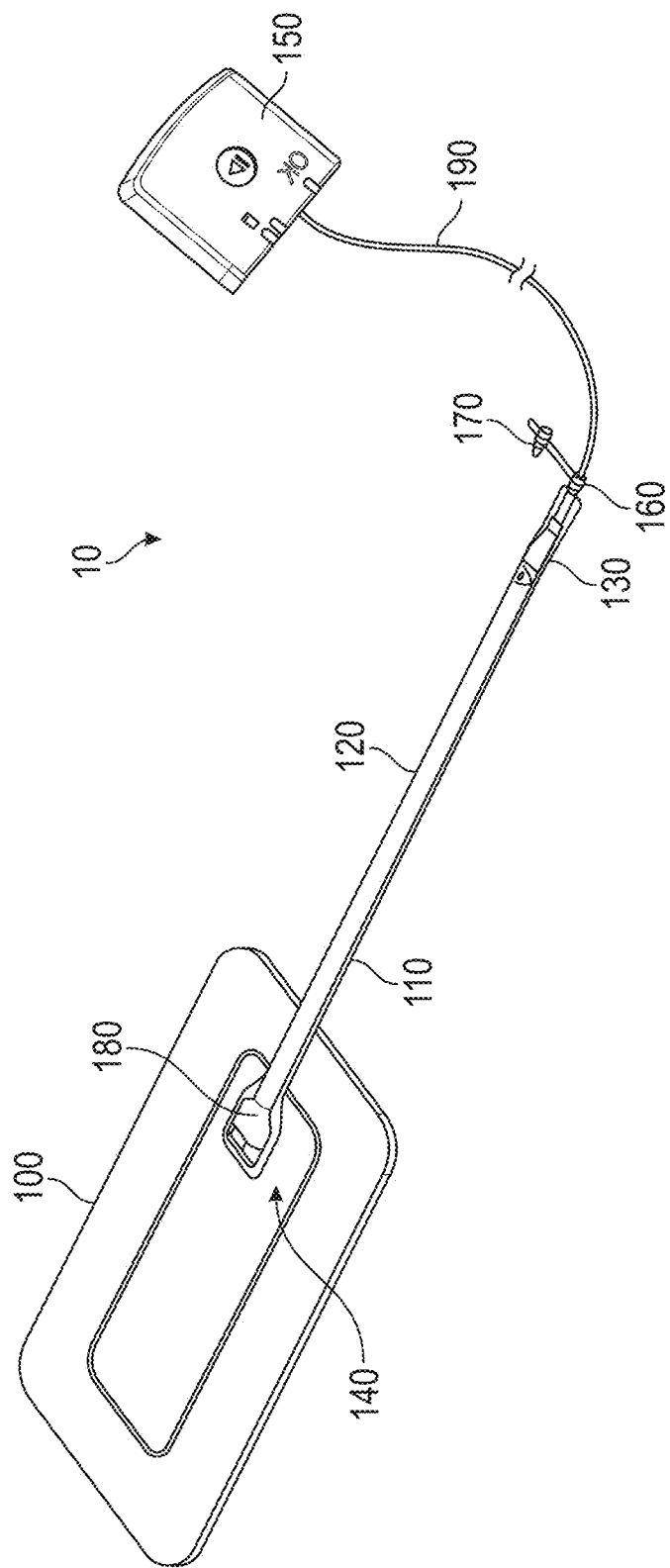
FIG. 1D illustrates an example negative pressure wound treatment system employing a flexible fluidic connector and a wound dressing capable of absorbing and storing wound exudate.

FIGS. 1C-1D illustrate examples of a negative pressure wound treatment system 10 employing a wound dressing 100 in conjunction with a fluidic connector 110. Here, the fluidic connector 110 may comprise an elongate conduit, for example, a bridge 120 having a proximal end 130 and a distal end 140, and an applicator 180 at the distal end 140 of the bridge 120. An optional coupling 160 can be disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The negative pressure wound treatment system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some cases, such as illustrated in FIGS. 1A-1B, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the wound dressing 100 is placed over a suitably-prepared wound, which may in some cases be filled with a wound packing material such as foam or gauze. The applicator 180 of the fluidic connector 110 has a sealing surface that is placed over an aperture in the wound dressing 100 and is sealed to the top surface of the wound dressing 100. Either before, during, or after connection of the fluidic connector 110 to the wound dressing 100, the pump 150 is connected via the tube 190 to the coupling 160, or is connected directly to the coupling 160 or to the bridge 120. The pump is then activated, thereby supplying negative pressure to the wound. Application of negative pressure may be applied until a desired level of healing of the wound is achieved.

Figure 1E:
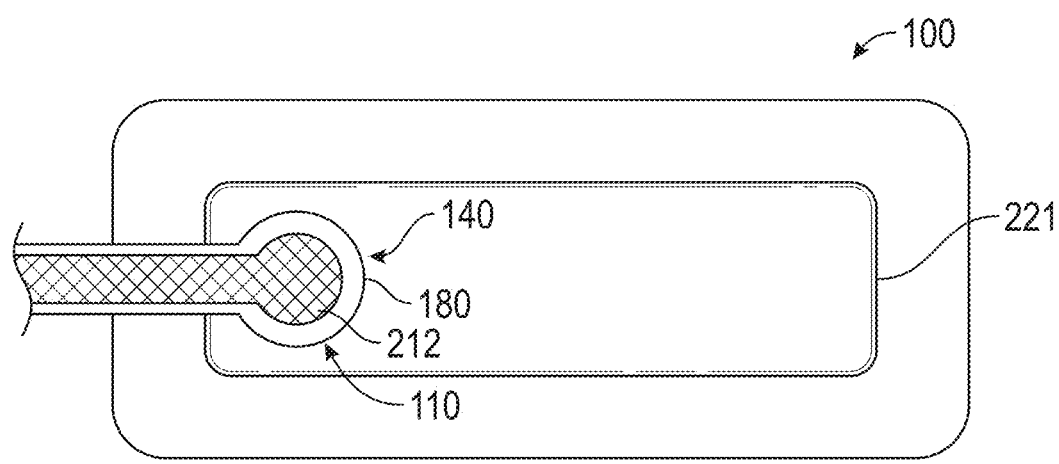
FIG. 1E illustrates an example negative pressure wound treatment system employing a flexible fluidic connector and a wound dressing capable of absorbing and storing wound exudate.

As shown in FIG. 1E, the fluidic connector 110 comprises an enlarged distal end, or head 140 that is in fluidic communication with the wound dressing 100 as will be described in further detail below. In one example, the enlarged distal end has a round or circular shape. The head 140 is illustrated here as being positioned near an edge of the wound dressing 100, but may also be positioned at any location on the dressing. For example, some examples may provide for a centrally or off-centered location not on or near an edge or corner of the wound dressing 100. In some cases, the wound dressing 100 may comprise two or more fluidic connectors 110, each comprising one or more heads 140, in fluidic communication therewith. In an example, the head 140 may measure 30 mm along its widest edge. The head 140 forms at least in part the applicator 180, described above, that is configured to seal against a top surface of the wound dressing.

Figure 1F:
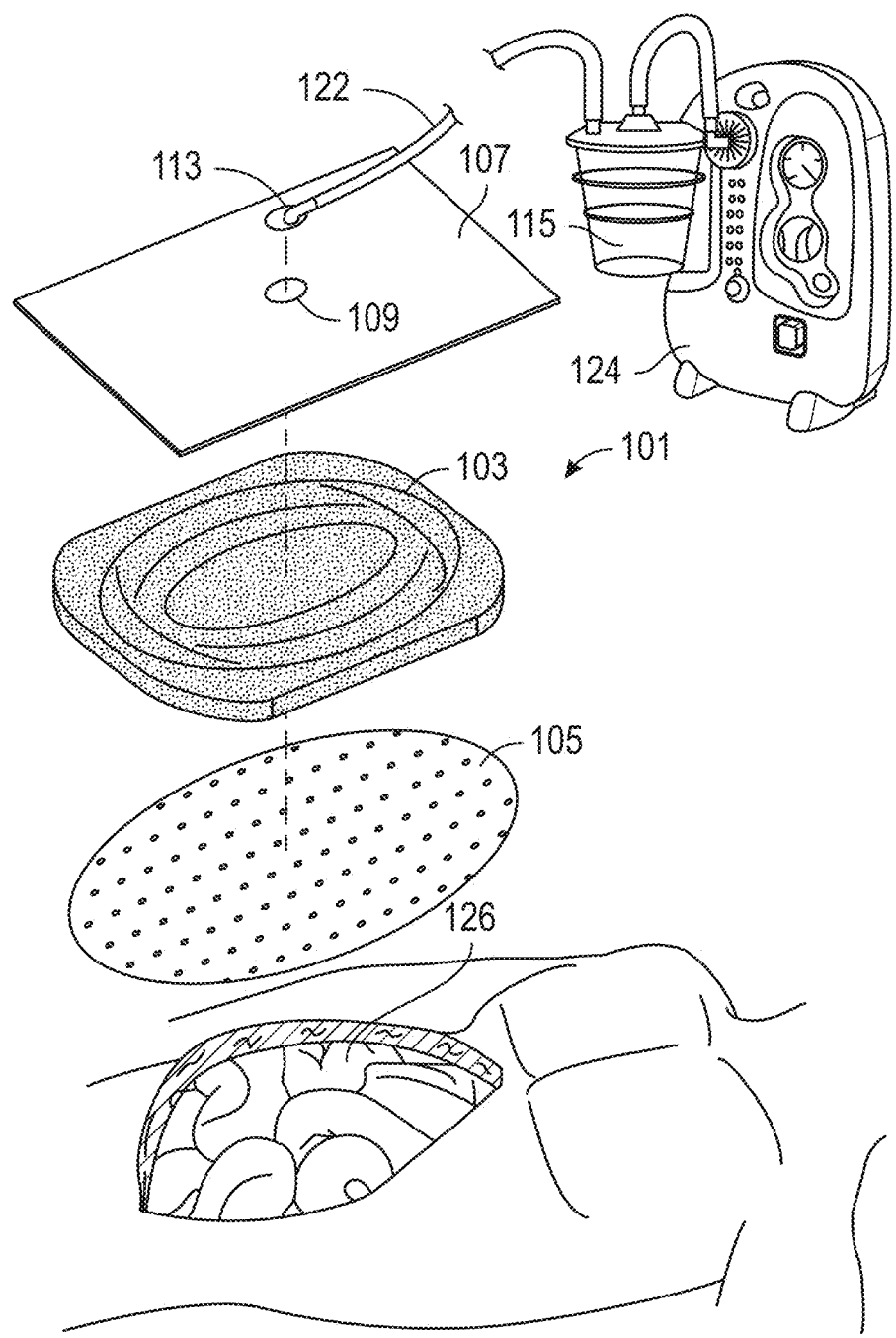
FIG. 1F illustrates of an example negative pressure wound treatment system.

Turning to FIG. 1F, treatment of other wound types, such as larger abdominal wounds, with negative pressure in certain examples uses a negative pressure treatment system 101 as illustrated schematically here. In this example, a wound 126, illustrated here as an abdominal wound, may benefit from treatment with negative pressure. Such abdominal wounds may be a result of, for example, an accident or due to surgical intervention. In some cases, medical conditions such as abdominal compartment syndrome, abdominal hypertension, sepsis, or fluid edema may require decompression of the abdomen with a surgical incision through the abdominal wall to expose the peritoneal space, after which the opening may need to be maintained in an open, accessible state until the condition resolves. Other conditions may also necessitate that an opening—particularly in the abdominal cavity—remain open, for example if multiple surgical procedures are required (possibly incidental to trauma), or there is evidence of clinical conditions such as peritonitis or necrotizing fasciitis.

In cases where there is a wound, particularly in the abdomen, management of possible complications relating to the exposure of organs and the peritoneal space is desired, whether or not the wound is to remain open or if it will be closed. Therapy, preferably using the application of negative pressure, can be targeted to minimize the risk of infection, while promoting tissue viability and the removal of deleterious substances from the wound. The application of reduced or negative pressure to a wound has been found to generally promote faster healing, increased blood flow, decreased bacterial burden, increased rate of granulation tissue formation, to stimulate the proliferation of fibroblasts, stimulate the proliferation of endothelial cells, close chronic open wounds, inhibit burn penetration, or enhance flap and graft attachment, among other things. It has also been reported that wounds that have exhibited positive response to treatment by the application of negative pressure include infected open wounds, decubitus ulcers, dehisced incisions, partial thickness burns, and various lesions to which flaps or grafts have been attached. Consequently, the application of negative pressure to a wound 106 can be beneficial to a patient.

Accordingly, certain examples provide for a wound contact layer 105 to be placed over the wound 126. The wound contact layer can also be referred to as an organ protection layer or a tissue protection layer. Preferably, the wound contact layer 105 can be a thin, flexible material which will not adhere to the wound or the exposed viscera in close proximity. For example, polymers such as polyurethane, polyethylene, polytetrafluoroethylene, or blends thereof may be used. In one example, the wound contact layer is permeable. For example, the wound contact layer 105 can be provided with openings, such as holes, slits, or channels, to allow the removal of fluids from the wound 126 or the transmittal of negative pressure to the wound 126. Additional examples of the wound contact layer 105 are described in further detail below.

Certain examples of the negative pressure wound treatment system 10 may also use a porous wound filler 103, which can be disposed over the wound contact layer 105. This pad 103 can be constructed from a porous material, for example foam, that is soft, resiliently flexible, and generally conformable to the wound 126. Such a foam can include an open-celled and reticulated foam made, for example, of a polymer. Suitable foams include foams composed of, for example, polyurethane, silicone, and polyvinyl alcohol. Preferably, this pad 103 can channel wound exudate and other fluids through itself when negative pressure is applied to the wound. Some pads 103 may include preformed channels or openings for such purposes. In certain examples, the pad 103 may have a thickness between about one inch and about two inches. The pad may also have a length of between about 16 and 17 inches, and a width of between about 11 and 12 inches. In other examples, the thickness, width, or length can have other suitable values. Other examples of wound fillers that may be used in place of or in addition to the pad 103 are discussed in further detail below.

Preferably, a drape 107 is used to seal the wound 126. The drape 107 can be at least partially liquid impermeable, such that at least a partial negative pressure may be maintained at the wound. Suitable materials for the drape 107 include, without limitation, synthetic polymeric materials that do not significantly absorb aqueous fluids, including polyolefins such as polyethylene and polypropylene, polyurethanes, polysiloxanes, polyamides, polyesters, and other copolymers and mixtures thereof. The materials used in the drape may be hydrophobic or hydrophilic. Examples of suitable materials include Transeal® available from DeRoyal and OpSite® available from Smith & Nephew. In order to aid patient comfort and avoid skin maceration, the drapes in certain examples are at least partly breathable, such that water vapor is able to pass through without remaining trapped under the dressing. An adhesive layer may be provided on at least a portion the underside of the drape 107 to secure the drape to the skin of the patient, although certain examples may instead use a separate adhesive or adhesive strip. Optionally, a release layer may be disposed over the adhesive layer to protect it prior to use and to facilitate handling the drape 107; in some cases, the release layer may be composed of multiple sections.

The negative pressure wound treatment system 10 can be connected to a source of negative pressure, for example a pump. One example of a suitable pump is the Renasys EZ pump available from Smith & Nephew. The drape 107 may be connected to the source of negative pressure via a conduit 122. The conduit 122 may be connected to a port 113 situated over an aperture 109 in the drape 107, or else the conduit 122 may be connected directly through the aperture 109 without the use of a port. In a further alternative, the conduit may pass underneath the drape and extend from a side of the drape. U.S. Pat. No. 7,524,315 discloses other similar aspects of negative pressure systems and is hereby incorporated by reference in its entirety and should be considered a part of this specification.

In many applications, a container or other storage unit 115 may be interposed between the source of negative pressure 124 and the conduit 122 so as to permit wound exudate and other fluids removed from the wound to be stored without entering the source of negative pressure. Certain types of negative pressure sources—for example, peristaltic pumps—may also permit a container 115 to be placed after the source of negative pressure 124. Some examples may also use a filter to prevent fluids, aerosols, and other microbial contaminants from leaving the container 115 or entering the source of negative pressure 124. Further examples may also include a shut-off valve or occluding hydrophobic or oleophobic filter in the container to prevent overflow; other examples may include sensing means, such as capacitive sensors or other fluid level detectors that act to stop or shut off the source of negative pressure should the level of fluid in the container be nearing capacity. At the pump exhaust, it may also be preferable to provide an odor filter, such as an activated charcoal canister.

Figure 1G:
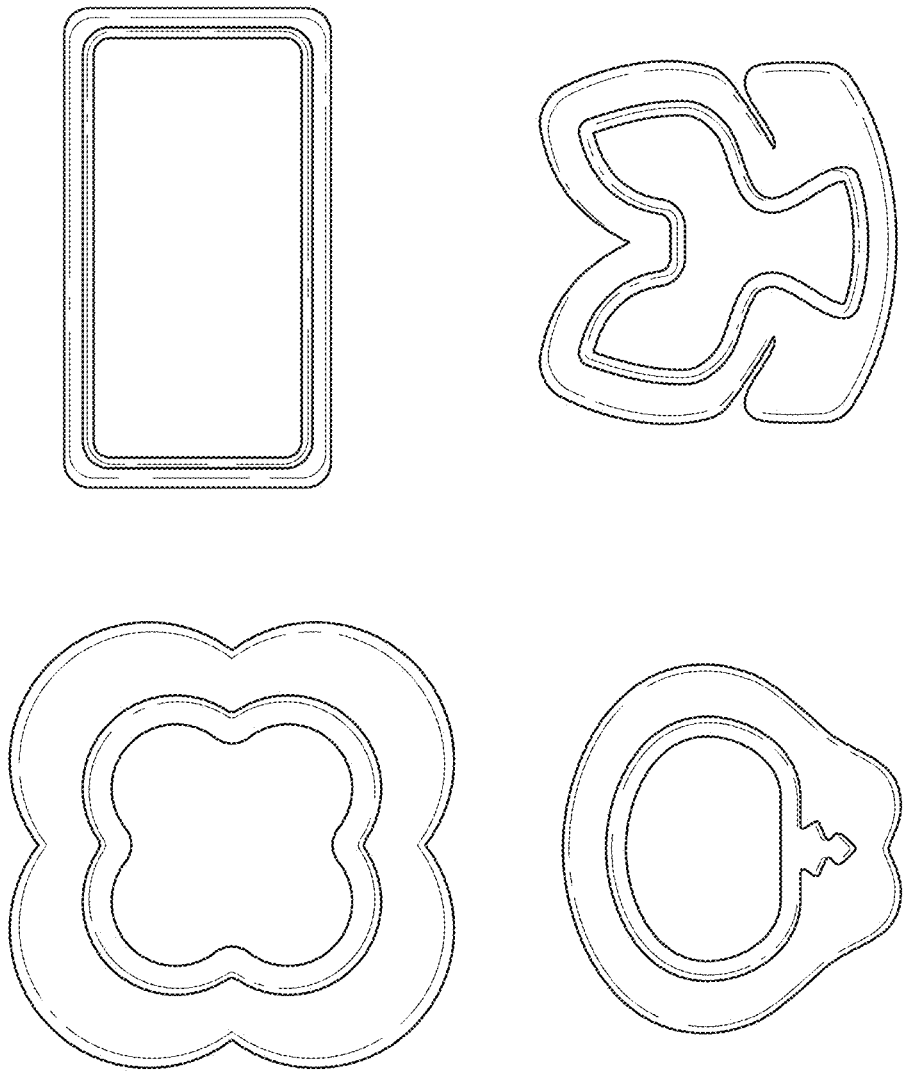
FIG. 1G illustrates an example wound treatment system employing a wound dressing capable of absorbing and storing wound exudate to be used without negative pressure.

FIG. 1G illustrates various examples of a wound dressing that can be used for healing a wound without negative pressure. As shown in the dressings of FIG. 1G, the wound dressings can have multiple layers similar to the dressings described with reference to FIGS. 1C-1F except the dressings of FIG. 1G do not include a port or fluidic connector. The wound dressings of FIG. 1G can include a cover layer and wound contact layer as described herein. The wound dressing can include various layers positioned between the wound contact layer and cover layer. For example, the dressing can include one or more absorbent layers or one or more transmission layers as described herein with reference to FIGS. 1C-1F. Additionally, some examples related to wound treatment comprising a wound dressing described herein may also be used in combination or in addition to those described in U.S. Application Publication No. 2014/0249495, filed May 21, 2014, entitled "WOUND DRESSING AND METHOD OF TREATMENT" the disclosure of which are hereby incorporated by reference in its entirety, including further details relating to examples of wound dressings, the wound dressing components and principles, and the materials used for the wound dressings.

Wound Dressing with Sensors

A wound dressing that incorporates a number of sensors can be utilized in order to monitor characteristics of a wound as it heals. Collecting data from the wounds that heal well, and from those that do not, can provide useful insights towards identifying measurands to indicate whether a wound is on a healing trajectory.

Figure 2:
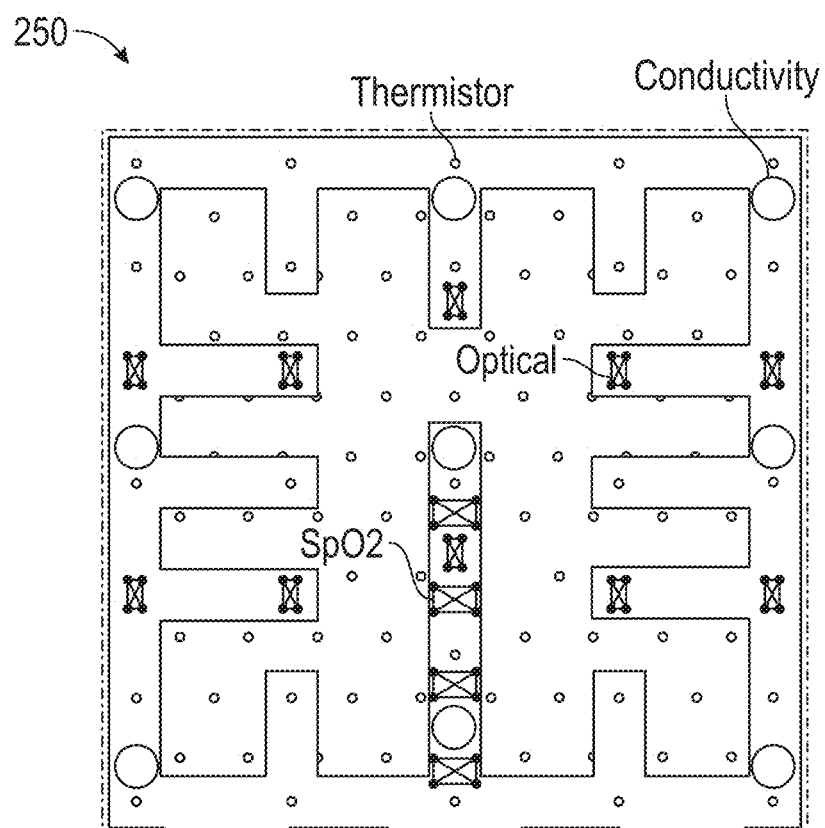
FIG. 2 illustrates an example sensor array illustrating the sensor placement incorporated into a wound dressing.
Figure 3A:
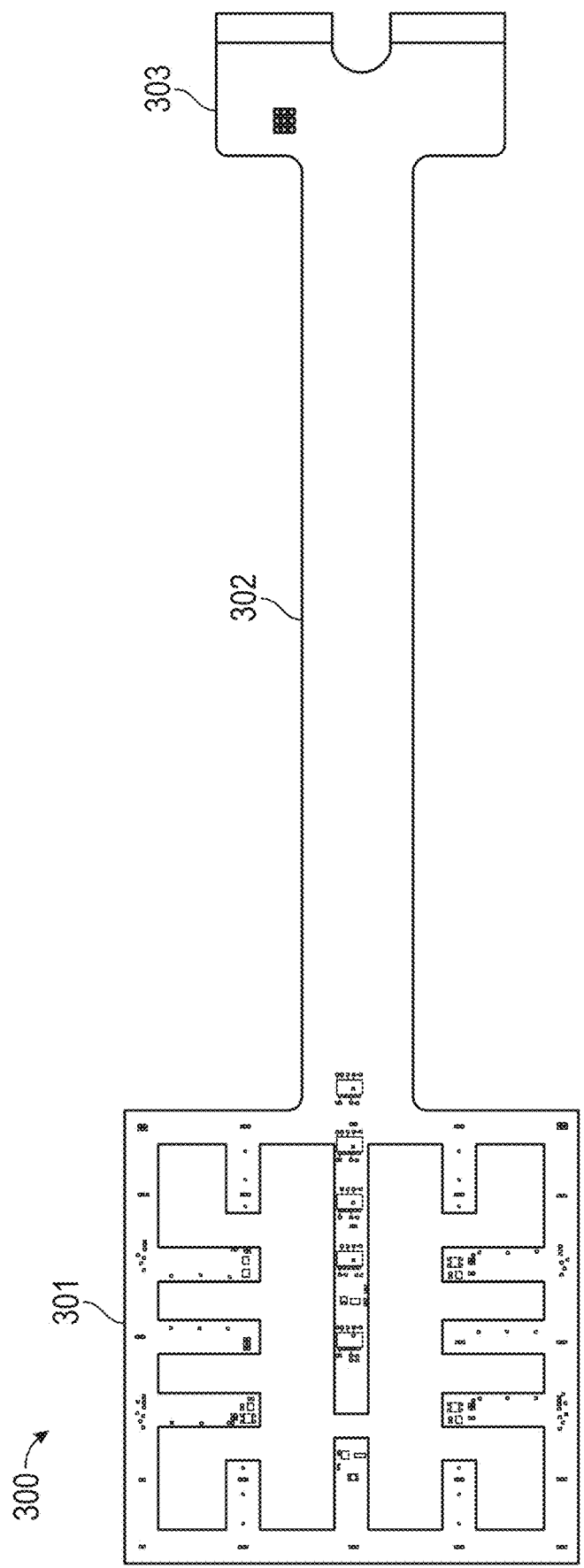
FIG. 3A illustrates an example flexible sensor array including a sensor array portion, a tail portion, and a connector pad end portion.

In some implementations, a number of sensor technologies can be used in wound dressings or one or more components forming part of an overall wound dressing assembly. For example, as illustrated in FIGS. 2 and 3D, which depict example wound dressings 250 and 320 with sensor arrays, one or more sensors can be incorporated onto or into a wound contact layer, which may be a perforated wound contact layer as shown in FIG. 3D. The wound contact layer in FIGS. 2 and 3D is illustrated as having a square shape, but it will be appreciated that the wound contact layer may have other shapes such as rectangular, circular, oval, etc. In some cases, the sensor integrated wound contact layer can be provided as an individual material layer that is placed over the wound area and then covered by a wound dressing assembly or components of a wound dressing assembly, such as gauze, foam or other wound packing material, a superabsorbent layer, a drape, a fully integrated dressing like the Pico or Allevyn Life dressing, etc. In other cases, the sensor integrated wound contact layer may be part of a single unit dressing such as described herein.

The sensor-integrated wound contact layer can be placed in contact with the wound and will allow fluid to pass through the contact layer while causing little to no damage to the tissue in the wound. The sensor-integrated wound contact layer can be made of a flexible material such as silicone and can incorporate antimicrobials or other therapeutic agents known in the art. In some cases, the sensor-integrated wound contact layer can incorporate adhesives that adhere to wet or dry tissue. In some cases, the sensors or sensor array can be incorporated into or encapsulated within other components of the wound dressing such as the absorbent layer or spacer layer described above.

As shown in FIGS. 2 and 3D, five sensors can be used, including, for instance, sensors for temperature (such as, 25 thermistor sensors, in a 5×5 array, ~20 mm pitch), oxygen saturation or SpO2 (such as, 4 or 5 SpO2 sensors, in a single line from the center of the wound contact layer to the edge thereof, 10 mm pitch), tissue color (such as, 10 optical sensors, in 2×5 array, ~20 mm pitch; not all 5 sensors in each row of the array need be aligned), pH (such as, by measuring color of a pH sensitive pad, optionally using the same optical sensors as for tissue color), and conductivity (such as, 9 conductivity contacts, in a 3×3 array, ~40 mm pitch). As shown in FIG. 3A, the SpO2 sensors can be arranged in a single line from the center of or near the center of the wound contact layer to the edge of the wound contact layer. The line of SpO2 sensors can allow the sensor to take measurements in the middle of the wound, at the edge or the wound, or on intact skin to measure changes between the various regions. In some cases, the wound contact layer or sensor array can be larger than the size of the wound to cover the entire surface area of the wound as well as the surrounding intact skin. The larger size of the wound contact layer or sensor array and the multiple sensors can provide more information about the wound area than if the sensor was only placed in the center of the wound or in only one area at a time.

The sensors can be incorporated onto flexible circuit boards formed of flexible polymers including polyamide, polyimide (PI), polyester, polyethylene naphthalate (PEN), polyetherimide (PEI), along with various fluropolymers (FEP) and copolymers, or any material known in the art. The sensor array can be incorporated into a two-layer flexible circuit. In some cases, the circuit board can be a multi-layer flexible circuit board. In some cases, these flexible circuits can be incorporated into any layer of the wound dressing. In some cases, a flexible circuit can be incorporated into a wound contact layer. For example, the flexible circuit can be incorporated into a wound contact layer similar to the wound contact layer described with reference to FIG. 1B. The wound contact layer can have cutouts or slits that allow for one or more sensors to protrude out of the lower surface of the wound contact layer and contact the wound area directly.

In some cases, the sensor-integrated wound contact layer can include a first and second wound contact layer with the flexible circuit board sandwiched between the two layers of wound contact layer material. The first wound contact layer has a lower surface intended to be in contact with the wound and an upper surface intended to be in contact with flexible circuit board. The second wound contact layer has a lower surface intended to be in contact with the flexible circuit board and an upper surface intended to be in contact with a wound dressings or one or more components forming part of an overall wound dressing assembly. The upper surface of the first wound contact layer and the lower surface of the second wound contact layer can be adhered together with the flexible circuit board sandwiched between the two layers.

In some cases, the one or more sensors of the flexible circuit board can be fully encapsulated or covered by the wound contact layers to prevent contact with moisture or fluid in the wound. In some cases, the first wound contact layer can have cutouts or slits that allow for one or more sensors to protrude out of the lower surface and contact the wound area directly. For example, the one or more SpO2 sensors as shown in FIG. 3D are shown protruding out the bottom surface of the wound contact layer. In some cases, the SpO2 sensors can be mounted directly on a lower surface of the first wound contact layer. Some or all of the sensors and electrical or electronic component(s) may be potted or encapsulated (for example, rendered waterproof or liquid-proof) with a polymer, for example, silicon or epoxy based polymers. The encapsulation with a polymer can prevent ingress of fluid and leaching of chemicals from the components. In some cases, the wound contact layer material can seal the components from water ingress and leaching of chemicals.

In some cases, gathering and processing information related to the wound can utilize three components, including a sensor array, a control or processing module, and software. These components are described in more detail herein.

FIG. 3A illustrates a flexible sensor array circuit board 300 that includes a sensor array portion 301, a tail portion 302, and a connector pad end portion 303 according to some cases. The sensor array portion 301 can include the sensors and associated circuitry. The sensor array circuit board 300 can include a long tail portion 302 extending from the sensor array portion 301. The connector pad end portion 303 can be enabled to connect to a control module or other processing unit to receive the data from the sensor array circuit. The long tail portion 302 can allow the control module to be placed distant from the wound, such as for example in a more convenient location away from the wound.

Figure 3B:
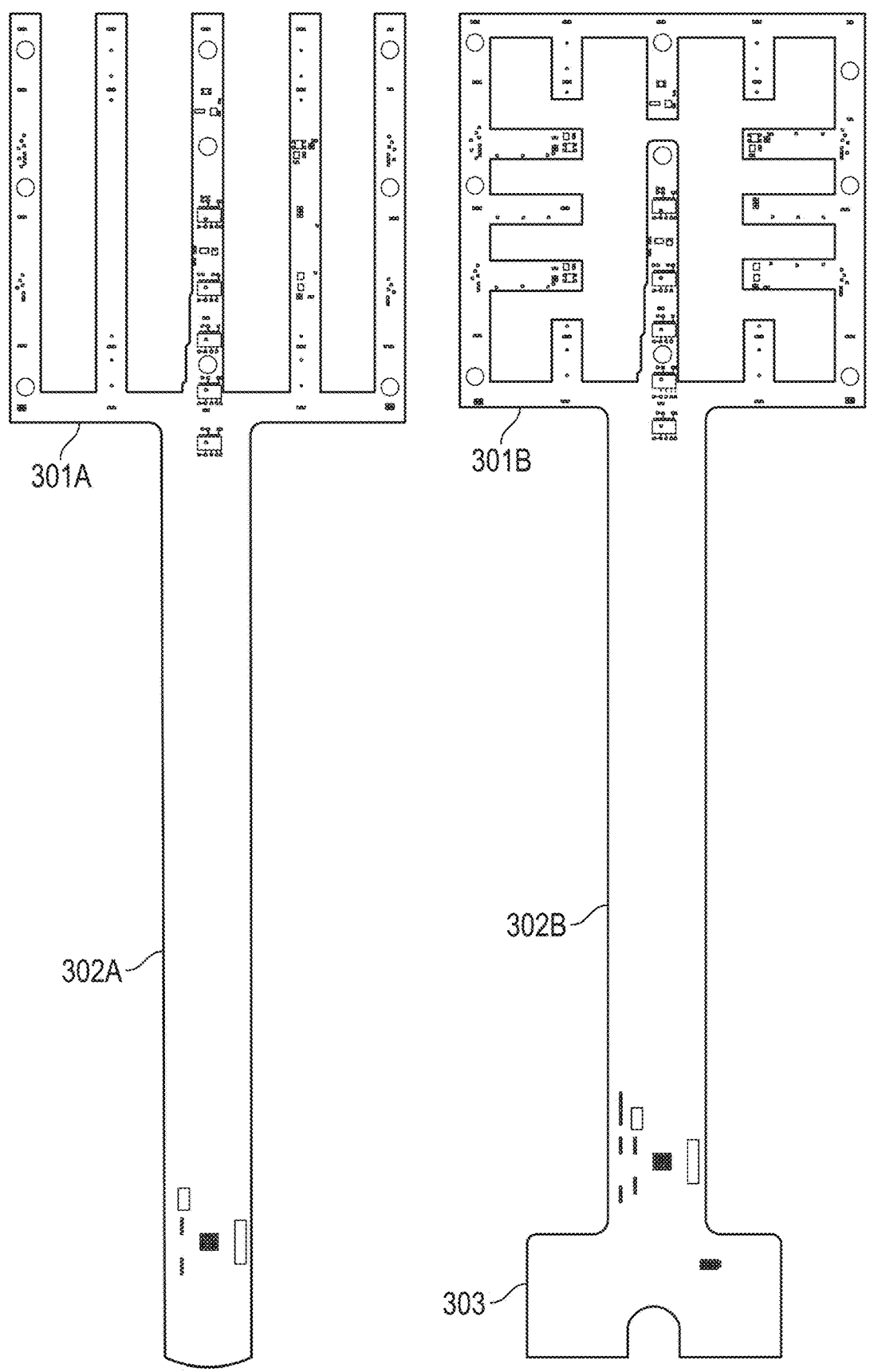
FIG. 3B illustrates example flexible circuit boards with different sensor array geometries.
Figure 3B:
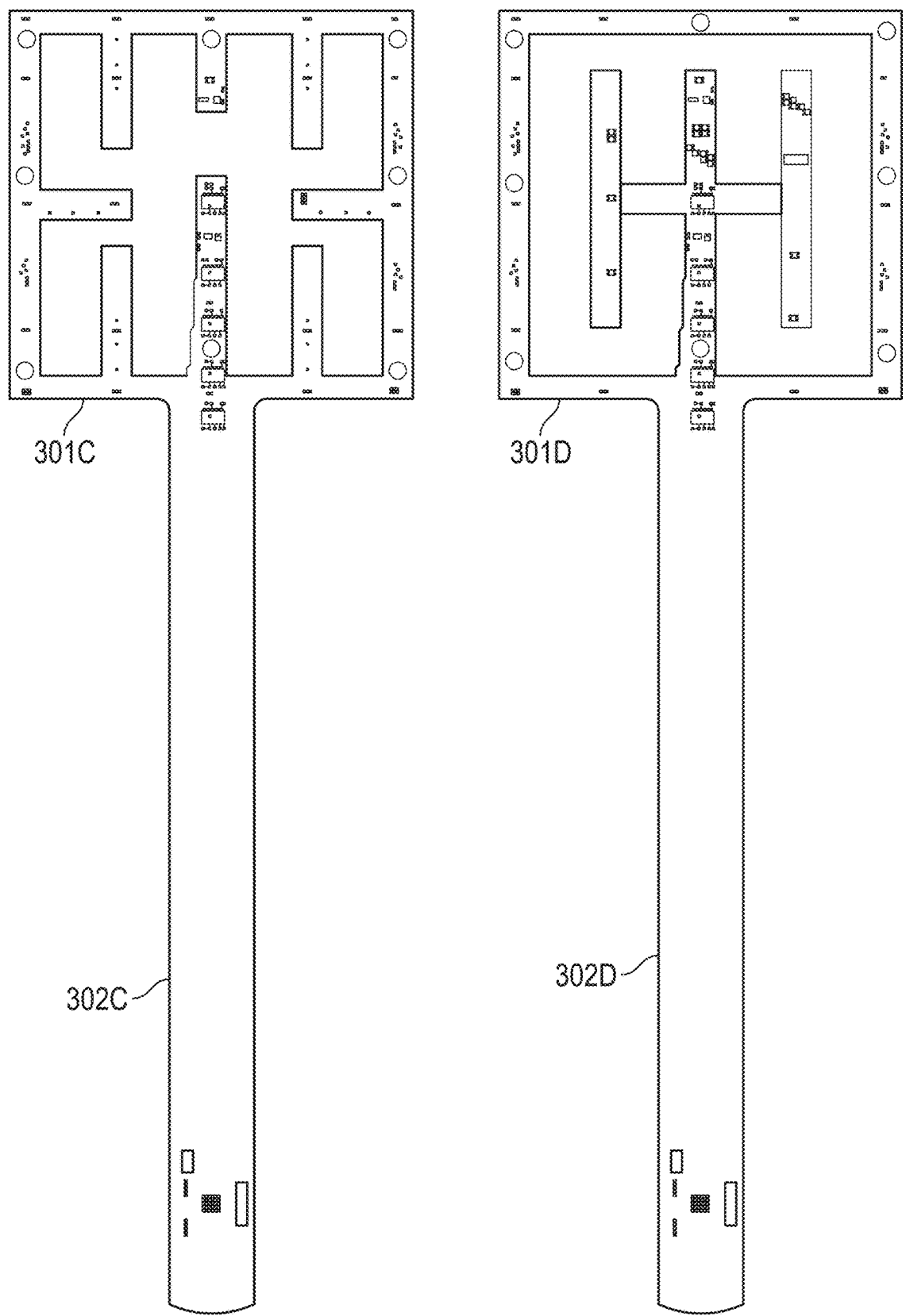

FIG. 3B illustrates examples of the flexible circuit boards with four different sensor array geometries 301A, 301B, 301C, and 301D. The illustrated examples include tail portions 302A, 302B. 302C, and 302D. In some cases, four different sensor array geometries shown can be implemented in flexible circuits. While FIG. 3B show four different sensor array formats and configurations, the design 301B and 302B also includes the connector pads end portion 303 configured to provide electrical or electronic connection between the sponsor array 301B and a control module. One or more of the designs in 301A, 301C, or 301D can also include a connector pads end portion, such as the portion 303, to allow flexible circuit boards 301A, 301C, or 301D to communicate with a control module or other processing unit. In some cases, the sensor array communicates with the control module wirelessly and the tail portion may be omitted.

Figure 3C:
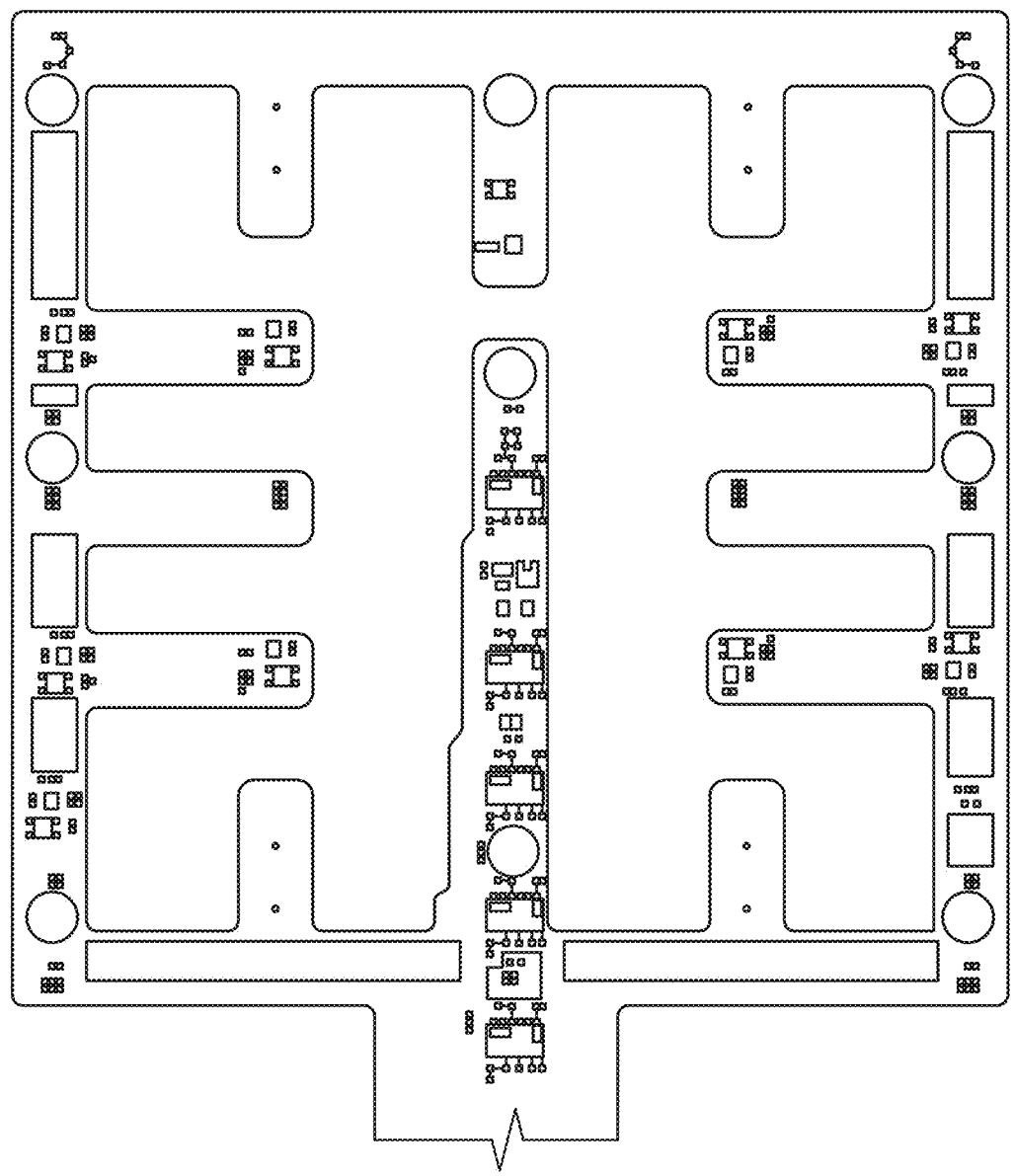
FIG. 3C illustrates the sensor array portion of the sensor array shown in FIG. 3B.
Figure 3D:
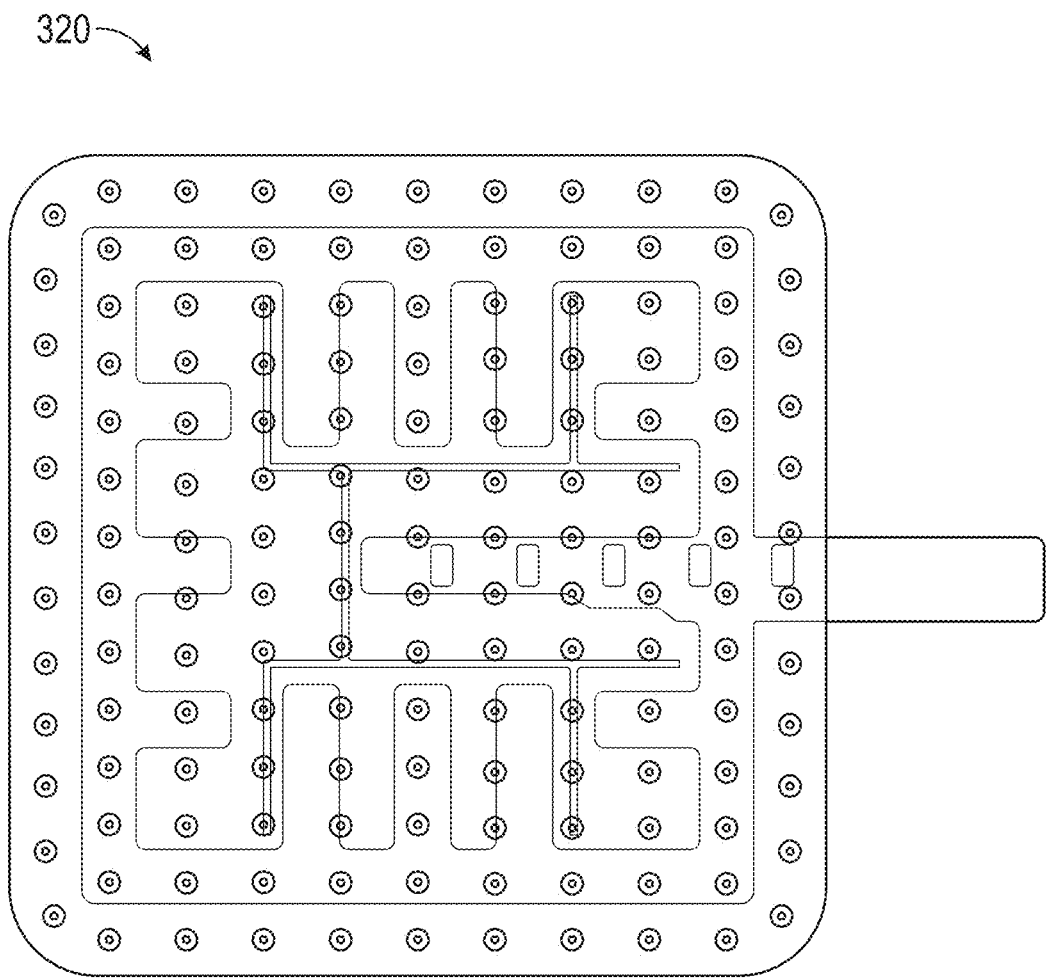
FIG. 3D illustrates an example flexible sensor array incorporated into a perforated wound contact layer.

FIG. 3C shows the sensor array portion 301B of the sensor array design shown of FIG. 3B in more detail. In any one or more of the examples of FIG. 2 or 3A-3D, the sensor array portion can include a plurality of portions that extend either around a perimeter of a wound dressing component such as a wound contact layer, or inward from an outer edge of the wound dressing component. For example, the illustrated examples include a plurality of linearly extending portions that may be parallel to edges of a wound dressing component, and in some cases, follow the entire perimeter of the wound dressing component. In some cases, the sensor array portion may comprise a first plurality of parallel linearly extending portions that are perpendicular to a second plurality of parallel linearly extending portions. These linearly extending portions may also have different lengths and may extend inward to different locations within an interior of a wound dressing component. The sensor array portion preferably does not cover the entire wound dressing component, so that gaps are formed between portions of the sensor array. As shown in FIG. 2, this allows some, and possibly a majority of the wound dressing component to be uncovered by the sensor array. For example, for a perforated wound contact layer as shown in FIGS. 2 and 3D, the sensor array portion 301 may not block a majority of the perforations in the wound contact layer. In some cases, the sensor array may also be perforated or shaped to match the perforations in the wound contact layer to minimize the blocking of perforations to fluid flow.

FIG. 3D illustrates an example flexible sensor array incorporated into a perforated wound contact layer 320. As is illustrated, the sensor array can be sandwiched between two films or wound contact layers. The wound contact layers can have perforations formed as slits or holes as described herein that are small enough to help prevent tissue ingrowth into the wound dressing while allowing wound exudate to flow into the dressing. In some cases, the wound contact layers can have one or more slits that increase flexibility of the wound contact layer with integrated sensor array. In some cases, one of the wound contact layers can have extra cut outs to accommodate the sensors so that they can contact the skin directly.

Connectivity for the sensor array can vary depending on the various sensors and sensor array designs utilized. In some cases, for example as shown in FIG. 3B, a total of 79 connections can be used to connect the components of the sensor array. The sensor arrays can be terminated in two parallel 40-way 0.5 mm pitch Flat Flexible Cable (FFC) contact surfaces, with terminals on the top surface, designed to be connected to an FFC connector such as Molex 54104-4031.

In some cases, one or more of thermistors, conductivity sensors, SpO2 sensors, or color sensors can be used on the sensor array to provide information relating to conditions of the wound. The sensor array and individual sensors can assist a clinician in monitoring the healing of the wound. The one or more sensors can operate individually or in coordination with each other to provide data relating to the wound and wound healing characteristics.

Temperature sensors can use thermocouples or thermistors to measure temperature. The thermistors can be used to measure or track the temperature of the underlying wound or the thermal environment within the wound dressing. The thermometry sensors can be calibrated and the data obtained from the sensors can be processed to provide information about the wound environment. In some cases, an ambient sensor measuring ambient air temperature can also be used to assist in eliminating problems associated with environment temperature shifts.

Optical sensors can be used to measure wound appearance using an RGB sensor (for example, a red, green, blue, and clear (RGBC) sensor or red, green blue, and white (RGBW) sensor) with an illumination source. In some cases, both the RGB sensor and the illumination source would be pressed up against the skin, such that light would penetrate into the tissue and take on the spectral features of the tissue itself.

Light propagation in tissue can be dominated by two major phenomena, scattering and attenuation. For attenuation, as light passes through tissue, its intensity may be lost due to absorption by various components of the tissue. Blue light tends to be attenuated heavily, whilst light at the red end of the spectrum tends to be attenuated least.

Scattering processes can be more complex, and can have various "regimes" which must be considered. The first aspect of scattering is based on the size of the scattering centre compared with the wavelength of incident light. If the scattering center is much smaller than the wavelength of light, then Rayleigh scattering can be assumed. If the scattering center is on the order of the wavelength of light, then a more detailed Mie scattering formulation must be considered. Another factor involved in scattering light is the distance between input and output of the scattering media. If the mean free path of the light (the distance between scattering events) is much larger than the distance travelled, then ballistic photon transport is assumed. In the case of tissue, scatting events are approximately 100 microns apart—so a 1 mm path distance would effectively randomize the photon direction and the system would enter a diffusive regime.

Ultra bright light emitting diodes (LEDs), an RGB sensor, and polyester optical filters can be used as components of the optical sensors to measure through tissue color differentiation. For example, because surface color can be measured from reflected light, a color can be measured from light which has passed through the tissue first for a given geometry. This can include color sensing from diffuse scattered light, from an LED in contact with the skin. In some cases, an LED can be used with an RGB sensor nearby to detect the light which has diffused through the tissue. The optical sensors can image with diffuse internal light or surface reflected light.

Additionally, the optical sensors can be used to measure autofluorescence. Autofluorescence is used because the tissue is absorbing light at one wavelength, and emitting at another. Additionally, dead tissue may not auto-fluoresce and so this could be a very strong indication as to if the tissue is healthy or not. Due to blue light (or even UV light) having such a short penetration depth, it may be very useful for example to have a UV light with a red sensitive photodiode nearby (or some other wavelength shifted band) to act as a binary test for healthy tissue, which would auto-fluoresce at a very particular wavelength.

Conductivity sensors can be used to determine the difference between living and dead tissue or to show a change in impedance due to a wound being opened up in morbid tissue. Conductivity sensors can include Ag/AgCl electrodes and an impedance analyser. The conductivity sensors can be used to measure the change of impedance of a region of wound growth by measuring the impedance of the surrounding tissue/area. In some cases, the sensor array can utilize conductivity sensors to measure the change in conductivity on perimeter electrodes due to a wound size or wound shape change. In some cases, the conductivity sensors can be used in the wound bed or on the perimeter of the wound.

In some cases, pH changing pads can be used as a pH sensor. A spectrometer and a broadband white light source can be used to measure the spectral response of the pH dye. The illumination and imaging can be provided on the surface of the wound dressing that is in contact with the wound and at the same side as the fluid application, the bottom surface. Alternatively, in some cases, the illumination and imaging source can be provided on the surface of the wound dressing opposite the bottom surface and away from fluid application or the top surface of the dressing.

In some cases, pulse oximetry SpO2 sensors can be used. To measure how oxygenated the blood is and the pulsatile blood flow can be observed. Pulse oximetry measurements work by taking a time resolved measurement of light absorption/transmission in tissue at two different optical wavelengths. When hemoglobin becomes oxygenated, its absorption spectrum changes with regards to non-oxygenated blood. By taking a measurement at two different wavelengths, one gains a ratio metric measure of how oxygenated the blood is.

The components in the sensor array can be connected through multiple connections. In some cases, the thermistors can be arranged in groups of five. Each thermistor is nominally 10 kΩ, and each group of five has a common ground. There are five groups of thermistors, giving a total of 30 connections. In some cases, there can be nine conductivity terminals. Each conductivity terminal requires one connection, giving a total of 9 connections. In some cases, there can be five SpO2 sensors. Each SpO2 sensor requires three connections, plus power and ground (these are covered separately), giving a total of 15 connections. In some cases, there can be 10 color sensors. Each color sensor comprises an RGB LED and an RGB photodiode. Each color sensor requires six connections, however five of these are common to every sensor, giving a total of 15 connections. Power and ground are considered separately. In some cases, there can be 5 pH sensors. The pH sensors can be a color-change discs, and can be sensed using the color sensors described above. Therefore, the pH sensors require no additional connections. There can be three power rails, and seven ground return signals, giving a total of 10 common connections. In some cases, the sensor array can include 25 thermistor (Murata NCP15WB473E03RC), 9 conductivity terminal, 5 SpO2 (ADPD144RI), 10 RGB LED (such as KPTF-1616RGBC-13), 10 RGB Color Sensor, 10 FET, a printed circuit board (PCB), and an assembly.

A control module can be used to interface with the sensor array. In some cases, the control module can contain a power source, such as one or more batteries, and electronics to drive the sensors. The control module can also log data at appropriate intervals and allow data transfer to an external computing device, such as a personal computer (PC). The control module can be customized to have various features depending on the sensors used in the sensor array and the data collected by the sensors. In some cases, the control module can be comfortable enough and small enough to be worn continuously for several weeks. In some cases, the control module can be positioned near the wound dressing or on the wound dressing. In some cases, the control module can be positioned in a remote location from the wound dressing and accompanying sensor array. The control module can communicate with the sensor array and wound dressing through electrical wires or through wireless communication whether positioned on the dressing, near the dressing, or remote from the wound dressing. In some cases, the control module can be adapted to be utilized with different sensor arrays and can enable easy replacement of the sensor array.

In some cases, the control module can include various requirements and combination of features including but not limited to the features listed in Table 1 below.

TABLE 1

OPTIONAL FEATURES FOR CONTROL MODULE 7 day operation from a single set of batteries
28 day local, non-volatile, storage capacity
Easy to charge, or to replace battery
Wireless link to PC/tablet (such as Bluetooth)
Wired link to PC (optional, micro-USB)
Drive electronics for thermistors
Drive electronics for conductivity sensors
Drive electronics for optical sensors
Drive electronics for SpO2 sensors
Power management TABLE 1-continued

OPTIONAL FEATURES FOR CONTROL MODULE

Figure 3E:
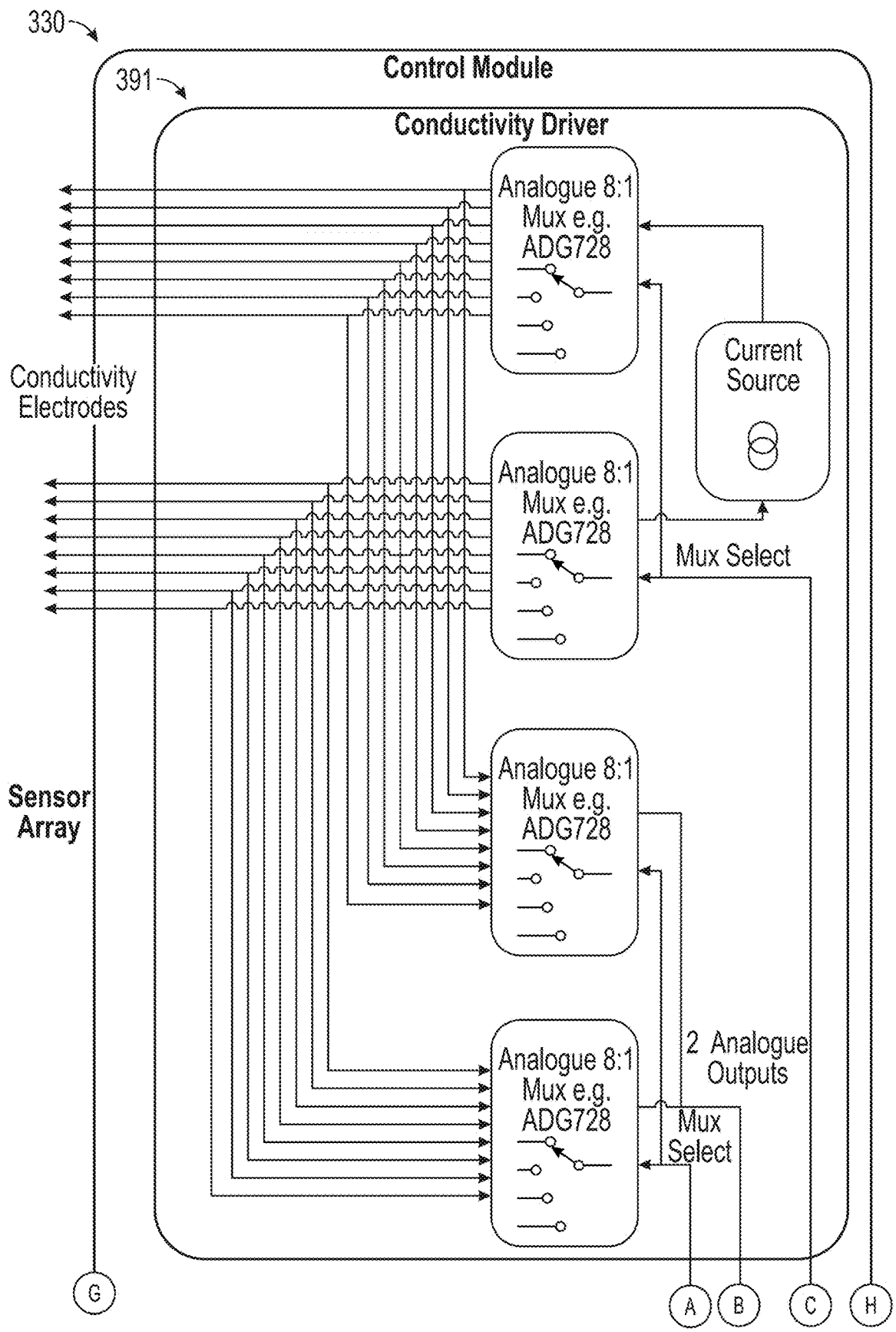
FIG. 3E illustrates an example control module.
Figure 3E:
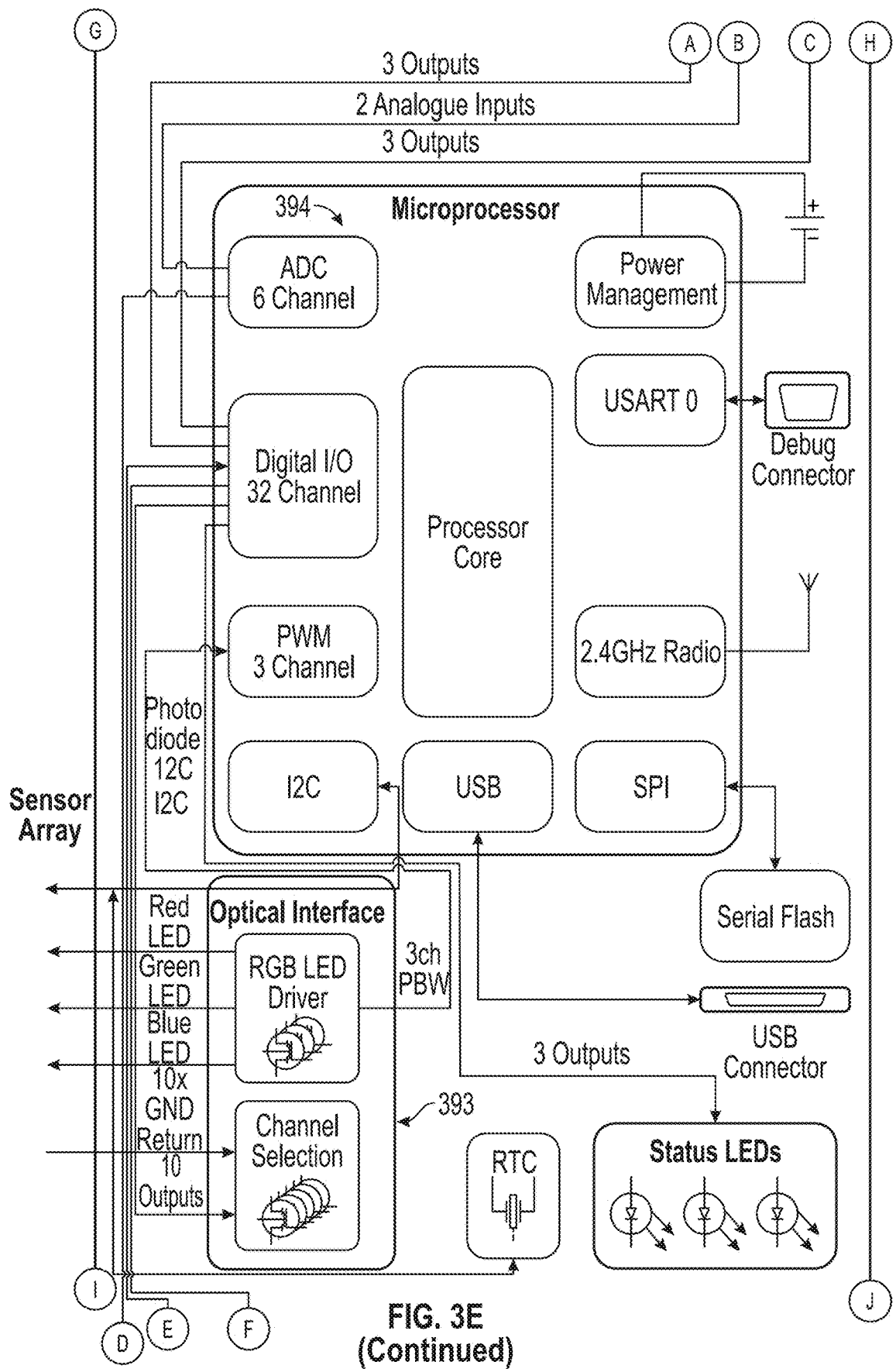
Figure 3E:
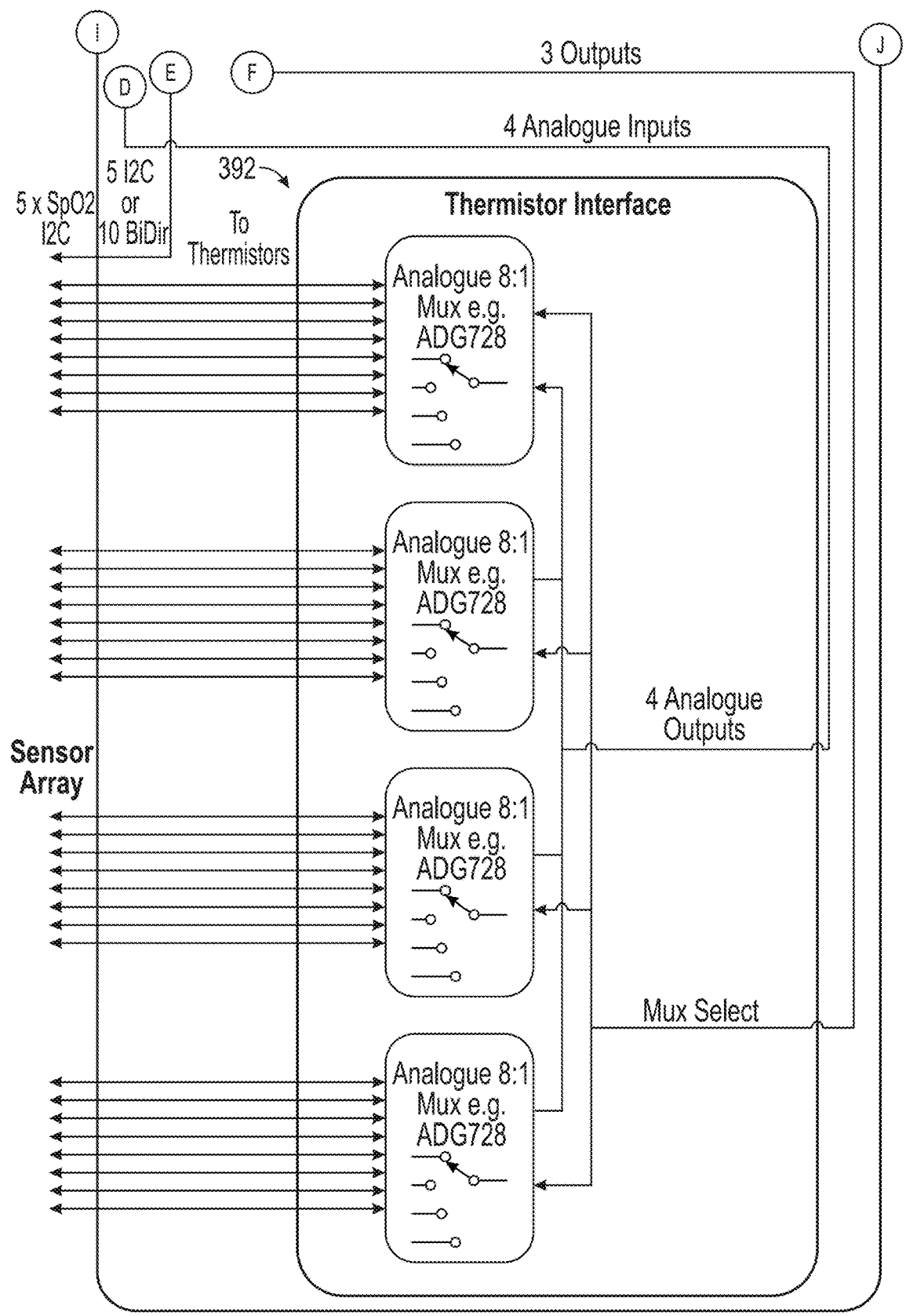

Real Time Clock (RTC) to allow accurate data logging, and correlation with other measurands
Ability to change sample rates and intervals (useful for SpO2) for each sensor
Indication of status via LED, such as (Green: Awake; Flashing green: Charging; Blue: Wireless link established; Flashing blue: Wireless data transfer; Yellow: Wired link established; Flashing yellow: Wired data transfer; Red: Battery low; Flashing red: Battery very low FIG. 3E illustrates a block diagram 330 of an example control module. The block diagram of the control module includes a conductivity driver box 391 displaying features of the conductivity driver. Box 392 shows the features of the thermistor interface and box 393 shows the features of the optical interface. The control module can include a controller or microprocessor with features similar to those shown in box 394. Real time clock (RTC), Status LEDs, USB connector, Serial Flash, and Debug Connector can be included as features of the control module as shown in FIG. 3E.

In some cases, the microprocessor can have one or more of the following features: 2.4 GHz or another suitable frequency radio (either integrated, or external); Supplied Bluetooth software stack; SPI interface; USB (or UART for external USB driver); I2C; 3 channel PWM; 32 GPIO; or 6-channel ADC. In some cases, the device can require at least 48 I/O pins or possibly more due to banking limitations. Bluetooth stack typically requires ~20 kB on-board Flash, so a minimum of 32 kB can be required. In some cases, 64 kB can be required if complex data processing is considered. The processor core can be ARM Cortex M4 or a similar processor core. In some cases, the parts can include ST's STM32L433LC or STM32F302R8, which would require an external radio, or NXP's Kinetis KW range including integrated radio.

In some cases, the control module can include a memory component where the amount of local storage depends on the sample rate and resolution of the sensors. For example, an estimated data requirement of 256 Mb (32 MB) can be met by using a serial Flash device from a number of manufacturers (Micron, Spansion).

The control module can utilize one or more analogue switches. In some cases, analogue switches with good on resistance and reasonable bandwidth can be used. For example, Analog Devices' ADG72 or NXP's NX3L4051HR can be used. Based on the initial system architecture, 8 of these will be required.

The control module can incorporate a power source, such as a battery. For example a 300 mWh/day battery can be used. For 7 days this is 2100 mWh. This could be provided by: a 10 days, non-rechargeable, ER14250 (14.5 mm diameter×25 mm) LiSOC12 cell; or a 7 days, rechargeable, Li 14500 (14.5 mm diameter×500 mm) Li-Ion.

The control module can incorporate a real time clock (RTC). The RTC can be chosen from any RTC devices with crystal. The control module can also include miscellaneous resistors, capacitors, connectors, charge controllers, and other power supplies.

The PCB of the control module can be a 4-layer board, approximately 50 mm×20 mm, or 25 mm×40 mm. The type of PCB used can be largely driven by connection requirements to sensor array.

The enclosure of the control module can be a two part moulding, with clip features to allow easy access for changing sensor arrays or batteries.

The data collected through the sensor array can be passed through the control module and processed by host software. The software may be executed on a processing device. The processing device can be a PC, tablet, smartphone, or other computer capable of running host software. The processing device executing the software can be in communication with the control module through electrical wires or through wireless communication. In some cases, the software may be configured to provide access to the data held on the control module, but not to perform big-data analysis. The host software can include an interface to the control module via Bluetooth or USB. In some cases, the host software can read the status of control module, download logged data from control module, upload sample rate control to control module, convert data from control module into format suitable for processing by big-data analysis engine, or upload data to cloud for processing by analysis engine.

The software may be developed for PC (Windows/Linux), tablet or smartphone (Android/iOS), or for multiple platforms.

In some cases, a source of negative pressure (such as a pump) and some or all other components of the topical negative pressure system, such as power source(s), sensor(s), connector(s), user interface component(s) (such as button(s), switch(es), speaker(s), screen(s), etc.) and the like, can be integral with the wound dressing. In some cases, the components can be integrated below, within, on top of, or adjacent to the backing layer. In some cases, the wound dressing can include a second cover layer or a second filter layer for positioning over the layers of the wound dressing and any of the integrated components. The second cover layer can be the upper most layer of the dressing or can be a separate envelope that enclosed the integrated components of the topical negative pressure system.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

Wound Therapy System with Multiple Power Sources

Figure 4:
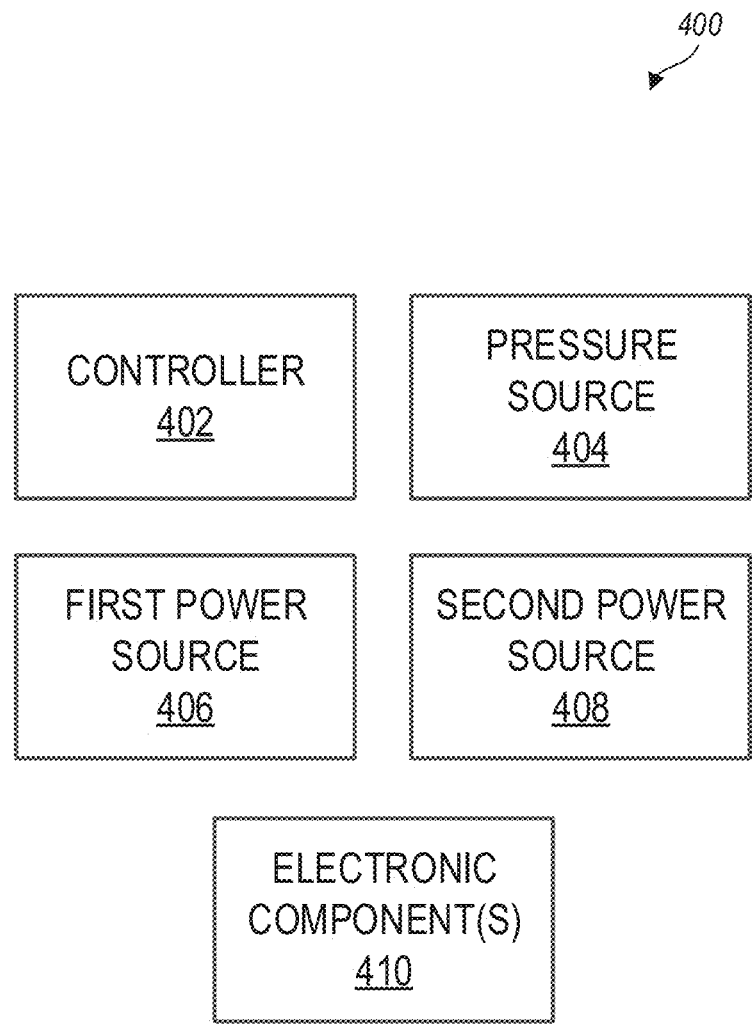
FIG. 4 illustrates an example wound treatment system.

FIG. 4 illustrates an example system 400 for providing therapy to a wound. The system 400 includes a controller 402, a pressure source 404, a first power source 406, a second power source 408, and electronic component(s) 410, any two or more of which can be electrically coupled with one another. The system 400 can include fewer or more components as desired. For example, in some cases, the system 400 may include one or any combination of two or more of the controller 402, the pressure source 404, the first power source 406, the second power source 408, or the electronic component(s) 410. As another example, the system 400 can include one or more additional controllers, pressure sources, power sources, or electronic components.

One or both of the first power source 406 or the second power source 408 can include an energy storage device configured to supply energy. For example, each the first power source 406 or the second power source 408 can be implemented as a battery, a capacitor, a capacitor-battery hybrid, a fuel-cell, or any combination thereof, among other energy storage devices.

One or both of the first power source 406 or the second power source 408 can include a battery. The size, shape, and characteristics of the battery can vary depending on the embodiment. For example, the battery can be one or more of various battery types including, but not limited to, a nickel cadmium battery, a nickel metal hydride battery, a lithium ion battery, a small sealed lead acid battery, an alkaline battery, or other suitable type of battery. Furthermore, the battery can be rechargeable or non-rechargeable.

The battery can be one or more of various shapes or sizes. For example, the battery can include a cylindrical battery, a coin-shaped cell, a rectangular battery, or other battery. Moreover, the battery can have a capacity or a rated voltage or current that is suitable for use in the system 400. For example, a battery can have a capacity falling within the range of 1 and 50 Watts, can be rated for a voltage falling within the range 1.25 V and 9 V (or more), and can be rated for a current falling within the range of 10 mA to several amps. In some cases, the battery can include multiple batteries, such as a bank of batteries. Each of the multiple batteries can be of the same or a different type, or can have the same or a different capacitance value.

One or both of the first power source 406 or the second power source 408 can include a capacitor. The size, shape, and general characteristics of the capacitor can vary depending on the embodiment. For example, the capacitor can be one or more of various types including, but not limited to, an electrolytic capacitor, a ceramic capacitor, a tantalum capacitor, a polycarbonate capacitor, a polyester capacitor, a silver mica capacitor, a glass dielectric capacitor, a polypropylene capacitor, polystyrene capacitor, or a super capacitor, among other types of capacitors. Furthermore, any of the one or more capacitors can be rechargeable.

The capacitor can have one or more of various capacitance values. For example, the capacitor can have relatively low capacitance values, ranging from 1 pF to a few microfarads. In addition or alternatively, the capacitor can have capacitance values as small as 1,000 pF or as large as 100 μF. Moreover, the capacitor can have capacitance values ranging up to about 1 mF or 1 F (non-limiting examples: 0.015 F, 0.022 F, 0.036 F, 0.047 F, 0.068 F, 0.1 F, 0.22 F, 0.33 F, 0.47 F, 0.7 F, or 0.85 F (+/−a few 10 or 100 mF)). Furthermore, in some implementations, the capacitor have a capacitance value at or exceeding a farad, such as, but not limited to, 1 F, 1.4 F, 1.5 F, 2.2 F, 3 F, 3.3 F, 4 F, 4.7 F, 10 F or more (+/−a few 100 mF). In some cases, the capacitor can include multiple capacitors, such as a bank of capacitors. Each of the multiple capacitors can be of the same or a different type, or can have the same or a different capacitance value.

The capacitor can include a super capacitor. Use of a super capacitor can be advantageous for one or several reasons. For example, in general, a super capacitor, as compared to other types of capacitors, can store more energy per unit volume (for example, 10 to 100 times). Moreover, a super capacitor can generally accept and deliver charge faster than batteries, and can generally tolerate more charge and discharge cycles than rechargeable batteries. In the event of a fault, a capacitor or a super capacitor can be less dangerous than a battery. Furthermore, in some cases, batteries are less suited to provide an impulse or high current than a capacitor or super capacitor.

One or both of the first power source 406 or the second power source 408 can be re-chargeable. For example, in some cases, the first power source 406 or the second power source 408 can be charged prior to, while, or after providing therapy to a wound of a patient. As another example, the first power source 406 or the second power source 408 can be charged prior to, while, or after positioning the wound dressing on the patient. For example, as described herein, one or more of the components of the system 400 can be included in, or supported by, a wound dressing such as wound dressing 100 or wound dressing 155. Such charging can be performed wirelessly, such as via inductive charging. In addition or alternatively, such charging can be performed via one or more energy harvesting techniques. One or more indications can be provided to indicate that one or both of the first or second power sources 406 or 408 has been charged, is charging, or has low or no charge. Prior to deployment on a patient, one or both of the first power source 406 or the second power source 408 can be stored without any power or configured with less than a full charge.

The electronic component(s) 410 can include one or more of various components of the system 400. For example, the electronic component(s) 410 can include, but are not limited to, wireless communication circuitry, one or more sensors (non-limiting examples: a pressure sensor, a nanosensor, a thermistor, a conductivity sensor, an SpO2 sensor, a pH sensor, a color sensor, an optical sensor, or electrical stimulator or stimulation component (non-limiting example: an electrode), or other sensing device), a real time clock (RTC), an LED (non-limiting example: a status LED), a user interface component (non-limiting examples: button(s), switch(es), speaker(s), screen(s), etc.), or the like. In some cases, although illustrated as separate in FIG. 4, the electronic component(s) 410 can even include the controller 402 or the pressure source 404, as well as one or more or all other electrical components of the system 400.

In some cases, the electronic component(s) 410 can include one or more active components, such as those which possess gain and can provide energy to the system 400 (non-limiting examples: a transistor, a battery, an amplifier, an integrated circuit, or the like.) In some cases, the electronic component(s) 410 can include one or more passive components, such as those which generally do not amplify or energize the energy of the signal associated with them (non-limiting examples: a resistor, an inductor, a capacitor, a diode, an LED, or the like).

The controller 402 can have features or capabilities similar to those of a controller or processor described herein, such as those features shown in, or described with respect to, box 394 of FIG. 3E. The controller 402 can be in electrical communication with or configured to control or operate any combination of the pressure source 404, first power source 406, second power source 408, or the electronic component(s) 410.

Furthermore, the controller 402 can monitor or determine an occurrence of one or more conditions associated with the system 400, such as one or more conditions associated with the first power source 406 or the second power source 408. Responsive to a first condition, the controller 402 can cause the first power source 406 to power the electronic component(s) 410 or can cause the second power source 408 to discontinue its powering of the electronic component(s) 410, or a combination thereof. Responsive to a second condition, the controller 402 can cause the second power source 408 to power the electronic component(s) 410 or can cause the first power source 406 to discontinue its powering of the electronic component(s) 410, or a combination thereof.

The pressure source 404 can provide negative pressure to a wound dressing that is positioned in contact with a wound of a patient. The pressure source 404 can include a pump, such as, without limitation, a rotary diaphragm pump or other diaphragm pump, a piezoelectric pump, a peristaltic pump, a piston pump, a rotary vane pump, a liquid ring pump, a scroll pump, a diaphragm pump operated by a piezoelectric transducer, or any other suitable pump or micropump or any combination thereof. In some cases, the pressure source 404 can be an example of one or more of a pump as described herein.

Figure 5:
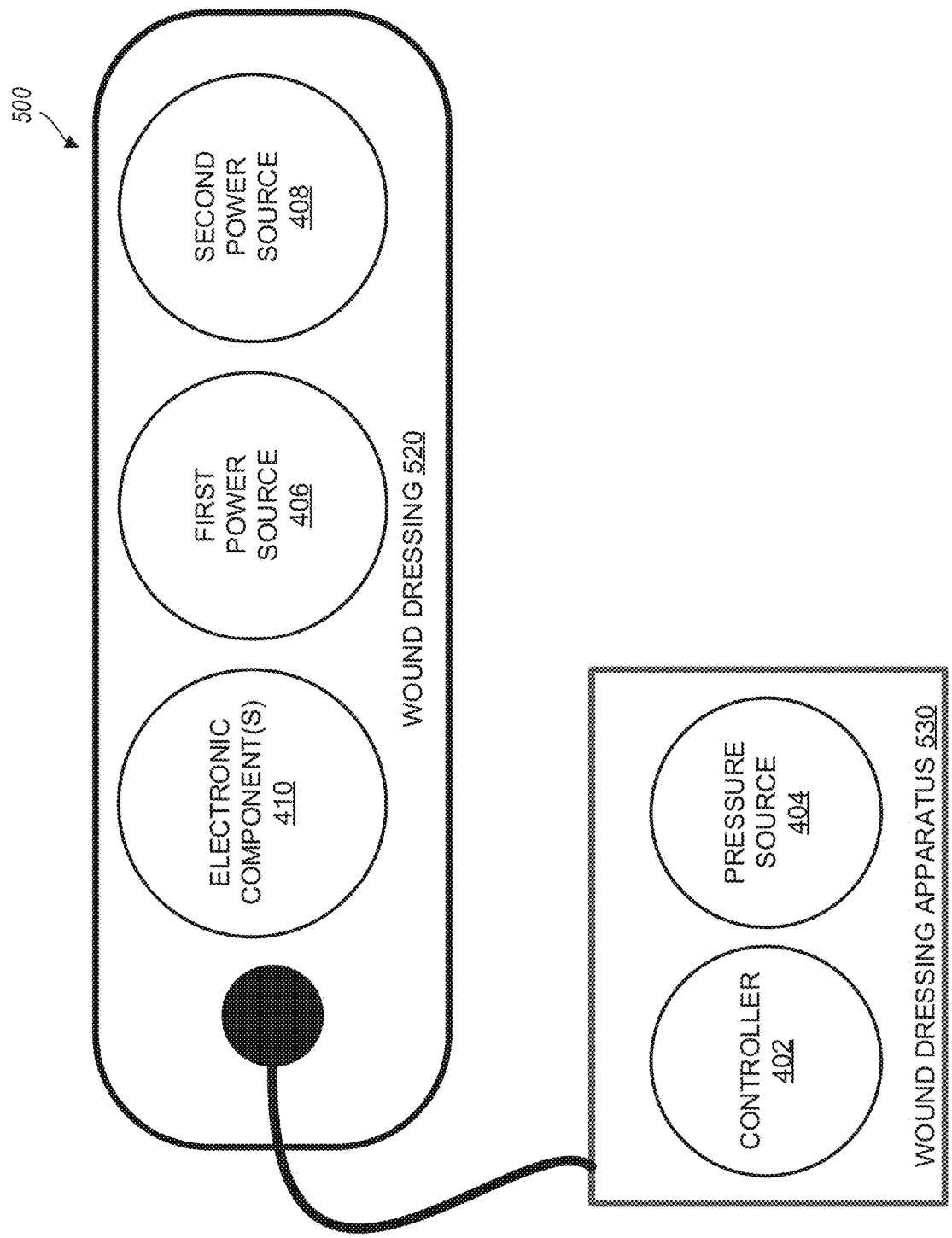
FIG. 5 illustrates an example configuration of the wound treatment system of FIG. 4.

FIG. 5 illustrates a system 500, which is an example configuration of the system 400 of FIG. 4. As described with respect to FIG. 4, the system 400 can include the controller 402, the pressure source 404, the first power source 406, the second power source 408, or the electronic component(s) 410.

Any of the controller 402, the pressure source 404, the first power source 406, the second power source 408, or the electronic component(s) 410 can be separate such that the system 500 includes two or more separate housings. For example, as illustrated in FIG. 5, the controller 402 and the pressure source 404 can be part of a wound dressing apparatus 530, while the first power source 406, the second power source 408, or the electronic component(s) 410 can be part of a wound dressing 520, which can be an example of the wound dressing 100 of FIGS. 1C-1E or the wound dressing 155 of FIG. 1B. Any of the separate housings can be placed apart from each other. Furthermore, one or more elements of each of the separate housings can communicate with one or more elements of the other separate housing via a wireless or wired connection.

Some or all of the components of the system 400 can be part of (non-limiting examples: integrated with, attached to, or embedded in) the wound dressing 520 (such as the wound dressing 100 of FIGS. 1C-1E or the wound dressing 155 of FIG. 1B). For example, in the illustrated example of FIG. 5, the first power source 406, the second power source 408, and the electronic component(s) 410 are part of the wound dressing 520. However, it will be understood that any combination of the controller 402, the pressure source 404, the first power source 406, the second power source 408, or the electronic component(s) 410 can be part of the wound dressing 520.

Some or all of the components of the system 400 can be part of (non-limiting examples: integrated with, attached to, or embedded in) the wound dressing apparatus 530 that can be different from the wound dressing 520. For example, in the illustrated example of FIG. 5, the controller 402 and the pressure source 404 are part of the wound dressing apparatus 530. However, it will be understood that any combination of the controller 402, the pressure source 404, the first power source 406, the second power source 408, or the electronic component(s) 410 can be part of the wound dressing apparatus 530.

As one example, the first power source 406 can include a battery and the second power source 408 can include a capacitor. The second power source 408 can act as a back-up or supplemental power supply to the first power source 406. For example, within a short time window of the first power source 406 dying or otherwise failing to satisfy a threshold battery charge, the system 400 can transfer at least some of the electrical load of the system 400 to the second power source 408 so that the second power source 408 provides power in addition to or in place of the first power source 406. As another example, within a short time window of the first power source 406 is experiencing a high energy demand, the system 400 can supplement at least some of the electrical load of the system 400 with power from the second power source 408 so that the second power source 408 provides power in addition to the first power source 406.

In some circumstances, it can be more important that certain components of the system 500 remain powered, while it may not be as important for other components to remain powered. Accordingly, in some cases, such as if one or both of the first power source 406 or the second power source 408 do not satisfy a threshold power, the system 500 can provide power to some components, while leaving other components unpowered, at least temporarily. In some cases, one or more of the components of the system (for example, any one or more of the pressure source 404, the first power source 406, the second power source 408, or the electronic component(s) 410) can be associated with a priority level.

As an example, the first power source 406 can provide power to all or most of the components of the system 500. Furthermore, a real-time clock of the system 400 (which may be maintained by the controller 402) can be associated with a first priority level, while other components of the system 500 (for example, any one or more of the pressure source 404, the first power source 406, the second power source 408, or the electronic component(s) 410) can be associated with one or more second priority levels. As the first power source 406 reduces in power such that it does not satisfy a threshold power, the system 500 can remove power from each of the components having the second priority level, while continuing to power the components of the first priority level. By discontinuing its provision of power to the second priority level components, the first power source 406 can conserve power for use in powering the first priority level components. Similarly, in some cases, the second power source 408 can act as a back up to the first power source 406. In some cases, the second power source 408 can provide backup power to the first priority level components, while not providing backup power to the second priority level components. In some cases, the second power source 408 can provide backup power to both the first priority level components and the second priority level components for a duration of time (for example, one second, one minute, five minutes, one hour, one day, or a shorter or longer duration) and then provide backup power to the first priority level components while not providing backup power to the second priority level components.

Some components of the system 400 can be better suited for charging or powering by the first power source 406. Moreover, other components of the system 400 can be better suited for charging or powering by second power source 408. For example, components (such as an electrode) that function using a large rush of electrical current, may be better suited for a capacitor. Accordingly, a capacitor of the second power source 408 can charge some components (for example, some, but not all, of the electronic component(s) 410) and a battery of the first power source 406 can charge different components (for example, different components of the electronic component(s) 410). In some cases, at least some components of the system 400 can be charged or powered by both the first power source 406 and the second power source 408, simultaneously or at distinct time intervals.

Continuing with the example, the system 400 can offer the benefits of both a battery and a capacitor. For example, a battery can provide advantages over a capacitor because a battery can have a greater energy density than a capacitor, among other things. Similarly, a capacitor can provide advantages over a battery because a capacitor can generally accept and deliver charge faster than a battery, can tolerate more charge and discharge cycles than rechargeable batteries, can be less dangerous in the event of a fault, and can provide an impulse or high current, among other things. Accordingly, by including both a battery (for example, in the first power source 406) and a capacitor (for example, in the second power source 408), the system 400 can offer the benefits of both a battery and a capacitor.

The second power source 408 can be rechargeable and the first power source 406 can charge the second power source 408. For example, while the first power source 406 is providing power to one or more components of the system 400, the first power source 406 can also provide power to the second power source 408. Alternatively, in some cases, one or more other components that are different from the first power source 406, such as a coin cell, can charge the second power source 408. Similarly, the first power source 406 can be rechargeable and the second power source 408 can charge the first power source 406.

Power Supply Control in Wound Monitoring or Therapy

Figure 6:
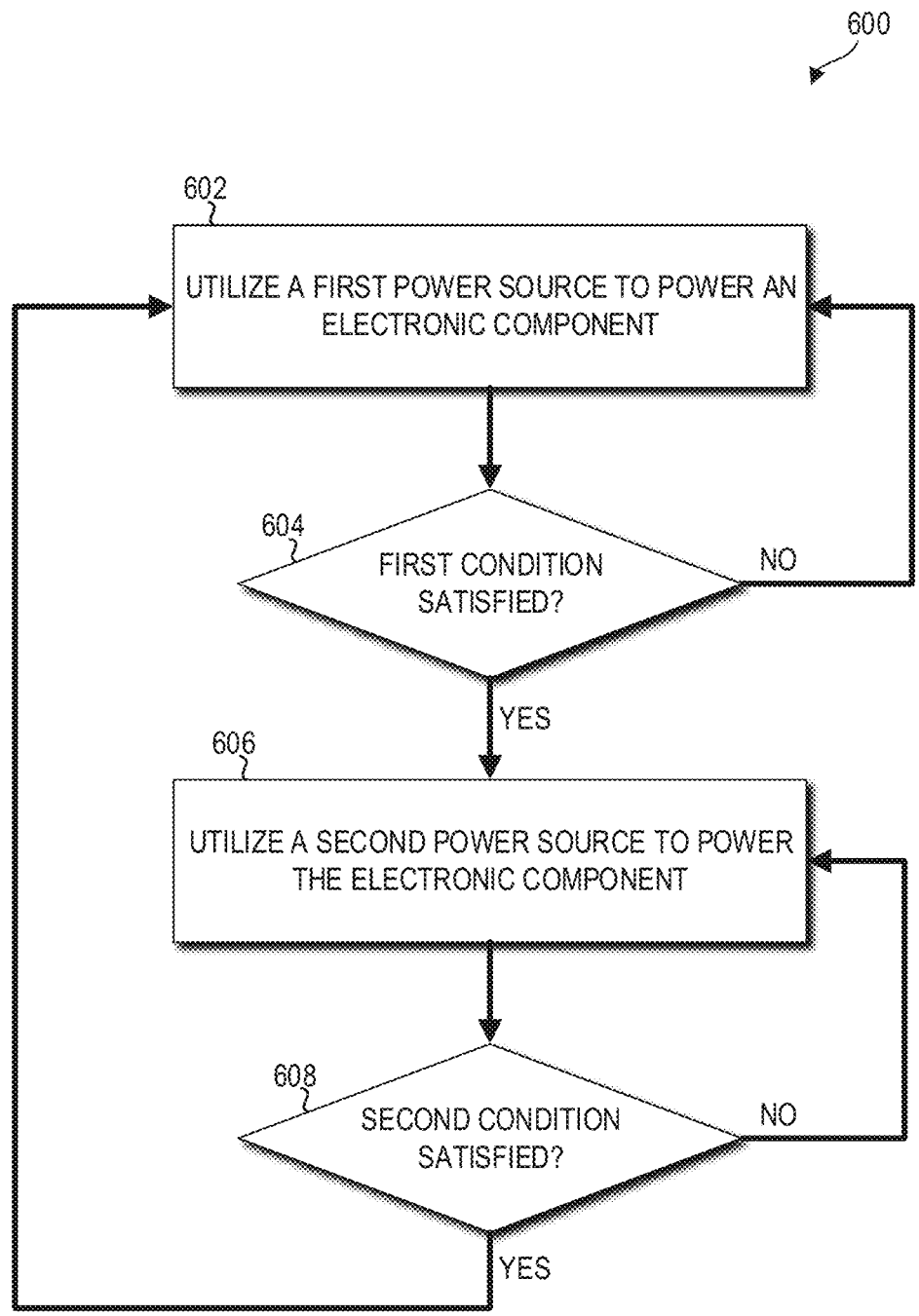
FIG. 6 is a flow diagram illustrative of an example routine for monitoring or providing therapy to a wound.

FIG. 6 is a flow diagram illustrative of an example of a routine 600 for monitoring or providing therapy to a wound. The elements outlined for routine 600 can be implemented by a system (such as the systems 102, 400, or 500), one or more computing devices or components that are associated with a system (non-limiting example: controller 402), a wound monitoring or therapy apparatus, or the like. For ease of reference, the routine 600 has been described as being performed by system 500. Furthermore, for convenience, the system 500 and the routine 600 are described in the context of the first power source 406 including a battery and the second power source 408 including a capacitor. However, other examples or configurations are possible.

At block 602, the battery of the first power source 406 supplies power to the electronic component(s) 410. The battery of the first power source 406 can electrically connect to the electronic component(s) 410. For example, so that the battery of the first power source 406 can supply power to the electronic component(s) 410, the controller 402 can electrically connect the battery of the first power source 406 to the electronic component(s) 410 with a switch or other component that makes or breaks an electrical connection between the battery of the first power source 406 and the electronic component(s) 410.

In some cases, at block 602, the electronic component(s) 410 may receive power from the battery of the first power source 406 and may not simultaneously receive power from another source of power, such as the capacitor of the second power source 408. In this way, the first power source 406 can supply power to the electronic component(s) 410 in place of the second power source 408. For example, the battery of the first power source 406 and the capacitor of the second power source 408 can power the electronic component(s) 410 at distinct time intervals, such that the first power source 406 does not provide power to the electronic component(s) 410 while the second power source 408 provides power to the electronic component(s) 410.

The controller 402 can cause the second power source 408 to discontinue supplying power to one or more of the electronic component(s) 410. For example, prior to block 602, the second power source 408 can be electrically connected and supplying power to the electronic component(s) 410. At block 602, the controller 402 can electrically disconnect the second power source 408 from the one or more of the electronic component(s) 410 with a switch or other component that makes or breaks an electrical connection between the second power source 408 and the electronic component(s) 410 so that the second power source 408 no longer supplies power to the electronic component(s) 410.

In some cases, at block 602, the electronic component(s) 410 simultaneously receive power from the first power source 406 and another source of power, such as the second power source 408. For example, the battery of the first power source 406 and the capacitor of the second power source 408 can provide power to the electronic component(s) 410 at one or more overlapping time intervals. The battery of the first power source 406 can, for instance, supply power to the electronic component(s) 410 while the capacitor of the second power source 408 is in a discharged state or otherwise includes a charge that does not satisfy a capacitor charge threshold.

The first power source 406 can power the electronic component(s) 410 and one or more other elements of the system 500, such as the controller 402, pressure source 404, capacitor of the second power source 408, or any combination thereof. For example, the battery of the first power source 406 can charge the capacitor of the second power source 408 while the battery of the first power source 406 provides power to the electronic component(s) 410.

At block 604, if a first condition is not satisfied, then the routine 600 returns to block 602, where the first power source 406 continues to power the electronic component(s) 410. On the other hand, if a first condition is satisfied, then the routine 600 proceeds to block 606.

The first condition can correspond to one or more characteristics or features of the first power source 406. As examples, the first condition can correspond to a capacity of the battery of the first power source 406, an amount of energy stored by the battery of the first power source 406, a voltage of the battery of the first power source 406, a temperature of the battery of the first power source 406, or a combination thereof. For instance, if the first condition corresponds to the voltage of the battery of the first power source 406, the first condition can be satisfied if the battery voltage satisfies a threshold battery voltage, or may not be satisfied if the battery voltage does not satisfy the threshold battery voltage.

Additionally or alternatively, the first condition can correspond to one or more characteristics or features of the second power source 408. As examples, the first condition can correspond to a capacitance of the capacitor of the second power source 408, a charge of the capacitor of the second power source 408, a voltage across the capacitor of the second power source 408, a temperature of the capacitor of the second power source 408, or a combination thereof. For instance, if the first condition corresponds to the charge of the capacitor of the second power source 408, the second condition can be satisfied if the charge of the capacitor of the second power source 408 charge satisfies a threshold charge, or may not be satisfied if the charge of the capacitor of the second power source 408 does not satisfy the threshold charge.

The controller 402 can monitor the one or more characteristics or features corresponding to the first condition to determine an occurrence of the first condition (for example, first condition satisfied) based at least on a comparison of a value associated with the monitored the characteristics or features to the threshold. Based on a determination that the threshold is satisfied, the controller 402 can cause the routine 600 to transition to block 606.

At block 606, the second power source 408 supplies power to one or more of the electronic component(s) 410. As described herein, the second power source 408 can electrically connect to the one or more of the electronic component(s) 410. For example, so that the capacitor of the second power source 408 can supply power to the one or more of the electronic component(s) 410, the controller 402 can electrically connect the capacitor of the second power source 408 to the electronic component(s) 410 with a switch or other component that makes or breaks an electrical connection between the capacitor of the second power source 408 and the electronic component(s) 410.

In some cases, at block 606, the electronic component(s) 410 may receive power from the second power source 408 and may not simultaneously receive power from the first power source 406. The second power source 408 can moreover supply power to the electronic component(s) 410 in place of the first power source 406. The controller 402 can, for instance, cause the first power source 406 to discontinue supplying power to the electronic component(s) 410 with a switch or other component that makes or breaks an electrical connection between the first power source 406 and one or more of the electronic component(s) 410 so that the first power source 406 no longer supplies power to the one or more of the electronic component(s) 410. The second power source 408 can in some cases supply power to the electronic component(s) 410 while the first power source 406 is in a discharged state or otherwise includes a voltage that does not satisfy a threshold voltage.

Additionally or alternatively, at block 606, the electronic component(s) 410 receive power from the second power source 408 and another source of power, such as the first power source 406. In some cases, at block 606, the first power source 406 can supply reduced power (as compared to block 602) to the electronic component(s) 410.

In some cases, at block 606, the second power source 408 may supply power to the electronic component(s) 410 and may not supply power to any of the controller 402, pressure source 404, or battery of the first power source 406. Alternatively, in some cases, the second power source 408 supplies power to the electronic component(s) 410 and one or more other elements of the system 500, such as the controller 402, the pressure source 404, the battery of the first power source 406, or any combination thereof. For example, the capacitor of the second power source 408 can charge the battery of the first power source 406 while the capacitor of the second power source 408 provides power to the electronic component(s) 410.

At block 608, if a second condition is not satisfied, then the routine 600 returns to block 606, where the second power source 408 continues to power the electronic component(s) 410. On the other hand, if a second condition is satisfied, then the routine 600 proceeds to block 608.

The second condition can correspond to one or more characteristics or features of the first power source 406. As examples, the second condition can correspond to a capacity of the battery of the first power source 406, an amount of energy stored by the battery of the first power source 406, a voltage of the battery of the first power source 406, a temperature of the battery of the first power source 406, or a combination thereof. For instance, if the second condition corresponds to the voltage of the battery, the first condition can be satisfied if the battery voltage satisfies a threshold battery voltage, or may not be satisfied if the battery voltage does not satisfy the threshold battery voltage.

The second condition can correspond to one or more characteristics or features of the second power source 408. As examples, the second condition can correspond to a capacitance of the capacitor of the second power source 408, a charge of the capacitor of the second power source 408, a voltage across the capacitor of the second power source 408, a temperature of the capacitor of the second power source 408, or a combination thereof. For instance, if the second condition corresponds to the charge of the capacitor of the second power source 408, the second condition can be satisfied if the charge of the capacitor of the second power source 408 charge satisfies a threshold charge, or may not be satisfied if the charge of the capacitor of the second power source 408 does not satisfy the threshold charge.

The controller 402 can monitor the one or more characteristics or features that correspond to the second condition to determine an occurrence of the second condition (for example, second condition satisfied) based at least on a comparison of a value associated with the monitored the characteristics or features to a threshold. Based on a determination that the threshold is satisfied, the controller 402 can cause the routine 600 to end or transition to block 602.

The various blocks described herein with respect to routine 600 can be implemented in a variety of orders, and that the routine 600 can implement one or more of the blocks concurrently or change the order, as desired. For example, the routine 600 can begin at block 606 rather than block 602. Furthermore, fewer, more, or different blocks can be used as part of the routine 600. For example, the routine 600 can omit certain blocks, such as, but not limited to, blocks 602, 604, 606, or 608. For example, the routine 600 can end responsive to a determination that the first condition is satisfied (block 604) or the second condition is satisfied (block 608).

The first power source 406 and the second power source 408 can power the electronic component(s) 410 at distinct time intervals, such that the first power source 406 does not power the electronic component(s) 410 while the second power source 408 powers the electronic component(s) or the second power source 408 does not power the electronic component(s) 410 while the first power source 406 powers the electronic component(s) 410. Alternatively, the first power source 406 and the second power source 408 can power the electronic component(s) 410 at overlapping time intervals, such that the first power source 406 can power the electronic component(s) 410 while the second power source 408 powers the electronic component(s) 410.

The first power source 406 can include a power source other than, or in addition to, a battery. For example, the first power source 406 can include a capacitor. Similarly, the second power source 408 can include a power source other than, or in addition to, a capacitor. For example, the second power source 408 can include a battery, such as a coin cell. Moreover, the subset of electronic component(s) 410 powered by the battery of the first power source 406 at block 602 can be different from the subset of electronic component(s) 410 powered by the capacitor of the second power source 408 at block 606. For example, the battery can power at least some electronic component(s) at block 606. Similarly, the capacitor of the second power source 408 can power at least some electronic component(s) at block 602.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the FIGS. Depending on the embodiment, certain of the steps described above may be removed, others may be added. For example, the actual steps or order of steps taken in the disclosed processes may differ from those shown in the FIG. Depending on the embodiment, certain of the steps described above may be removed, others may be added. For instance, the various components illustrated in the FIGS. may be implemented as software or firmware on a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A negative pressure wound therapy system comprising:
   a negative pressure source configured to provide negative pressure to a wound dressing positioned over a wound;
   an electronic control circuitry configured to operate the negative pressure source and communicate with a first set of electronic components and a second set of electronic components;
   a primary power source configured to provide power to the first set of electronic components; and
   a secondary power source comprising a capacitor configured to store energy and further configured to provide power to the second set of electronic components, wherein the second set of electronic components operates using a greater amount of current than the first set of electronic components,
   wherein the first set of electronic components does not receive power from the secondary power source and the second set of electronic components does not receive power from the primary power source during a first time interval, and
   wherein the electronic control circuitry is configured to:
      detect an occurrence of a first condition indicating that the primary power source is unable to provide sufficient power to the first set of electronic components for the first set of electronic components to operate; and
      responsive to detection of the occurrence of the first condition, cause the secondary power source to provide power to the first set of electronic components during a second time interval.

2. The negative pressure wound therapy system of claim 1, wherein the first condition corresponds to at least one of a remaining capacity or temperature of the primary power source.

3. The negative pressure wound therapy system of claim 1, wherein the primary power source comprises a battery.

4. The negative pressure wound therapy system of claim 1, wherein the first set of electronic components comprises at least one of a clock circuitry, a wireless communications device, a sensor, or an electrical stimulator.

5. The negative pressure wound therapy system of claim 1, wherein the second set of electronic components comprises one or more electrodes.

6. The negative pressure wound therapy system of claim 1, wherein the first set of electronic components comprises a sensor configured to be positioned proximate the wound and provide physiological data usable to monitor healing of the wound.

7. The negative pressure wound therapy system of claim 1, wherein the secondary power source is configured to be charged by a power source other than the primary power source.

8. The negative pressure wound therapy system of claim 1, wherein the secondary power source is configured to be charged by the primary power source.

9. The negative pressure wound therapy system of claim 1, wherein the electronic control circuitry is further configured to:
   detect an occurrence of a second condition indicating that the primary power source is able to provide sufficient power to the first set of electronic components for the first set of electronic components to operate; and
   responsive to detection of the occurrence of the second condition, cause the first set of electronic components to be powered by the primary power source and not the secondary power source during a third time interval.

10. The negative pressure wound therapy system of claim 9, wherein the second condition corresponds to at least one of a remaining capacity or temperature of the primary power source.

11. A medical device comprising:
   an electronic control circuitry comprising a plurality of electronic components that includes a first set of electronic components and a second set of electronic components;
   a primary power source configured to provide power to the first set of electronic components; and
   a secondary power source configured to store energy and further configured to provide power to the second set of electronic components,
   wherein the first set of electronic components does not receive power from the secondary power source and the second set of electronic components does not receive power from the primary power source during a first time interval, and
   wherein the electronic control circuitry is configured to:
      detect an occurrence of a first condition indicating that the primary power source is unable to provide sufficient power to the first set of electronic components for the first set of electronic components to operate; and
      responsive to detection of the occurrence of the first condition, cause the secondary power source to provide power to the first set of electronic components during a second time interval.

12. The medical device of claim 11, wherein the first condition corresponds to at least one of a remaining capacity or temperature of the primary power source.

13. The medical device of claim 11, wherein the primary power source comprises a battery and the secondary power source comprises a capacitor.

14. The medical device of claim 11, wherein the second set of electronic components operates using a greater amount of power than the first set of electronic components.

15. The medical device of claim 11, wherein the first set of electronic components comprises at least one of a clock circuitry, a wireless communications device, a sensor, or an electrical stimulator, and wherein the second set of electronic components comprises one or more electrodes.

16. The medical device of claim 11, wherein the first set of electronic components comprises a sensor configured to be positioned proximate a wound and provide physiological data usable to monitor healing of the wound.

17. The medical device of claim 11, wherein the secondary power source is configured to be charged by a power source other than the primary power source.

18. The medical device of claim 11, wherein the secondary power source is configured to be charged by the primary power source.

19. The medical device of claim 11, wherein the electronic control circuitry is further configured to:
  detect an occurrence of a second condition indicating that the primary power source is able to provide sufficient power to the first set of electronic components for the first set of electronic components to operate; and
  responsive to detection of the occurrence of the second condition, cause the first set of electronic components to be powered by the primary power source and not the secondary power source during a third time interval.

20. The medical device of claim 19, wherein the second condition corresponds to at least one of a remaining capacity or temperature of the primary power source.

* * * * *